(12) United States Patent
Weston

(10) Patent No.: US 7,708,724 B2
(45) Date of Patent: May 4, 2010

(54) REDUCED PRESSURE WOUND CUPPING TREATMENT SYSTEM

(75) Inventor: Richard Scott Weston, Carlsbad, CA (US)

(73) Assignee: Blue Sky Medical Group Incorporated, Memphis, TN (US)

(*) Notice: Subject to any disclaimer, the term of this patent is extended or adjusted under 35 U.S.C. 154(b) by 953 days.

(21) Appl. No.: 11/098,203

(22) Filed: Apr. 4, 2005

(65) Prior Publication Data

US 2005/0222528 A1 Oct. 6, 2005

Related U.S. Application Data

(60) Provisional application No. 60/559,727, filed on Apr. 5, 2004.

(51) Int. Cl.
*A61M 1/00* (2006.01)

(52) U.S. Cl. .................................. 604/304; 604/313

(58) Field of Classification Search ................ 604/304, 604/313–316, 74–76, 385.04–385.05, 385.25–385.28, 604/385.101, 380
See application file for complete search history.

(56) References Cited

U.S. PATENT DOCUMENTS

| 765,746 | A | 7/1904 | Miner |
| 846,674 | A | 7/1907 | Funk |
| 1,355,679 | A | 10/1920 | McConnell |

(Continued)

FOREIGN PATENT DOCUMENTS

CA 2049948 C 10/1990

(Continued)

OTHER PUBLICATIONS

Arnljots et al., "Irrigation Treatment in Split-Thickness Skin Grafting of Intractable Leg Ulcers," Scandinavian Journal of Plastic and Reconstructive Surgery, 1985, vol. 19, pp. 211-213.

(Continued)

*Primary Examiner*—Tanya Zalukaeva
*Assistant Examiner*—Lynne Anderson
(74) *Attorney, Agent, or Firm*—Knobbe Martens Olson & Bear LLP

(57) ABSTRACT

A reduced pressure treatment appliance is provided for treating a wound on the body of a patient. In some embodiments, the appliance comprises a cover, which is further comprised of a top cup member and an interface member. The interface member comprises flow control means, which permit exudate from the wound to flow through the flow control means into the volume under the cover, but not in the opposite direction. Also, in some embodiments, the top cup member is further comprised of a lid member, a cup body member, and lid attachment means to removably attach the lid member to the cup body member. In some of these embodiments, it is possible to access the wound for monitoring, treatment and other purposes without removing the cover from the body. In other embodiments, the wound treatment appliance also includes a vacuum system to supply reduced pressure to the site of the wound in the volume under the cover. In yet other embodiments, a suction bulb may be used to provide a source of reduced pressure to a cover that covers the wound. Finally, methods are provided for using various embodiments of the treatment appliance.

80 Claims, 4 Drawing Sheets

U.S. PATENT DOCUMENTS

| | | | |
|---|---|---|---|
| 1,355,846 A | 10/1920 | Rannells | |
| 1,385,346 A | 7/1921 | Taylor | |
| 1,585,104 A | 5/1926 | Montgomery | |
| 1,732,310 A | 10/1929 | Naibert | |
| 1,863,534 A | 6/1932 | Odell | |
| 1,936,129 A | 11/1933 | Fisk | |
| 2,122,121 A | 6/1938 | Tillotson | |
| 2,232,254 A | 2/1941 | Morgan | |
| 2,280,915 A | 4/1942 | Johnson | |
| 2,338,339 A | 1/1944 | La Mere et al. | |
| 2,366,799 A | 1/1945 | Luisada | |
| 2,367,690 A | 1/1945 | Purdy | |
| 2,547,758 A | 4/1951 | Keeling | |
| 2,969,057 A | 1/1961 | Simmons | |
| 3,026,526 A | 3/1962 | Montrose | |
| 3,026,874 A | 3/1962 | Stevens | |
| 3,042,041 A | 7/1962 | Jascalevich | |
| 3,217,707 A | 11/1965 | Werding | |
| 3,238,937 A | 3/1966 | Stein | |
| 3,286,711 A | 11/1966 | MacLeod | |
| 3,315,665 A | 4/1967 | MacLeod | |
| 3,367,332 A | 2/1968 | Groves | |
| 3,465,748 A | 9/1969 | Kravchenko | |
| 3,478,736 A | 11/1969 | Roberts et al. | |
| 3,486,504 A | 12/1969 | Austin, Jr. | |
| 3,568,675 A | 3/1971 | Harvey | |
| 3,572,340 A | 3/1971 | Lloyd et al. | |
| 3,610,238 A | 10/1971 | Rich, Jr. | |
| 3,682,180 A | 8/1972 | McFarlane | |
| 3,712,298 A | 1/1973 | Snowdon et al. | |
| 3,794,035 A | 2/1974 | Brenner | |
| 3,826,254 A | 7/1974 | Mellor | |
| 3,859,989 A | 1/1975 | Spielberg | |
| 3,874,387 A | 4/1975 | Barbieri | |
| 3,896,810 A | 7/1975 | Akiyama | |
| 3,908,664 A | 9/1975 | Loseff | |
| 3,938,540 A | 2/1976 | Holbrook et al. | |
| 3,954,105 A | 5/1976 | Nordby et al. | |
| 3,961,625 A | 6/1976 | Dillon | |
| 3,988,793 A | 11/1976 | Abitbol | |
| 3,993,080 A | 11/1976 | Loseff | |
| RE29,319 E | 7/1977 | Nordby et al. | |
| 4,080,970 A | 3/1978 | Miller | |
| 4,112,947 A | 9/1978 | Nehring | |
| 4,149,541 A | 4/1979 | Gammons et al. | |
| 4,169,563 A | 10/1979 | Leu | |
| 4,172,455 A | 10/1979 | Beaussant | |
| 4,224,945 A | 9/1980 | Cohen | |
| 4,250,882 A | 2/1981 | Adair | |
| 4,256,109 A | 3/1981 | Nichols | |
| 4,261,363 A | 4/1981 | Russo | |
| 4,275,721 A | 6/1981 | Olson | |
| 4,297,995 A | 11/1981 | Golub | |
| 4,373,519 A | 2/1983 | Errede et al. | |
| 4,382,441 A | 5/1983 | Svedman | |
| 4,392,853 A | 7/1983 | Muto | |
| 4,419,097 A | 12/1983 | Rowland | |
| 4,444,548 A | 4/1984 | Anderson et al. | |
| 4,459,139 A | 7/1984 | vonReis et al. | |
| 4,465,485 A | 8/1984 | Kashmer et al. | |
| 4,469,092 A | 9/1984 | Marshall et al. | |
| 4,475,909 A | 10/1984 | Eisenberg | |
| 4,480,638 A | 11/1984 | Schmid | |
| 4,525,166 A | 6/1985 | Leclerc | |
| 4,527,064 A | 7/1985 | Anderson | |
| 4,540,412 A | 9/1985 | Van Overloop | |
| 4,543,100 A | 9/1985 | Brodsky | |
| 4,573,965 A | 3/1986 | Russo | |
| 4,605,399 A | 8/1986 | Weston et al. | |
| 4,608,041 A | 8/1986 | Nielsen | |
| 4,624,656 A | 11/1986 | Clark et al. | |
| 4,640,688 A | 2/1987 | Hauser | |
| 4,710,165 A | 12/1987 | McNeil et al. | |
| 4,738,249 A | 4/1988 | Linman | |
| 4,743,232 A | 5/1988 | Kruger | |
| 4,753,231 A | 6/1988 | Lang et al. | |
| 4,759,354 A | 7/1988 | Quarfoot | |
| 4,764,167 A | 8/1988 | Tu | |
| 4,765,316 A | 8/1988 | Marshall | |
| 4,778,456 A | 10/1988 | Lokken | |
| 4,820,265 A | 4/1989 | DeSatnick et al. | |
| 4,820,284 A | 4/1989 | Hauri | |
| 4,834,110 A | 5/1989 | Richard | |
| 4,836,192 A | 6/1989 | Abbate | |
| 4,838,883 A | 6/1989 | Matsuura | |
| 4,840,187 A | 6/1989 | Brazier | |
| 4,841,962 A | 6/1989 | Berg et al. | |
| 4,851,545 A | 7/1989 | Song et al. | |
| 4,863,449 A | 9/1989 | Therriault et al. | |
| 4,878,901 A | 11/1989 | Sachse | |
| 4,906,233 A | 3/1990 | Moriuchi et al. | |
| 4,917,112 A | 4/1990 | Kalt | |
| 4,921,488 A | 5/1990 | Maitz et al. | |
| 4,921,492 A | 5/1990 | Schultz | |
| 4,925,447 A | 5/1990 | Rosenblatt | |
| 4,931,519 A | 6/1990 | Song et al. | |
| 4,941,882 A | 7/1990 | Ward et al. | |
| 4,950,483 A | 8/1990 | Ksander | |
| 4,953,565 A | 9/1990 | Tachibana et al. | |
| 4,969,880 A | 11/1990 | Zamierowski | |
| 4,969,881 A | 11/1990 | Viesturs | |
| 5,035,884 A | 7/1991 | Song et al. | |
| 5,086,764 A | 2/1992 | Gilman | |
| 5,100,396 A | 3/1992 | Zamierowski | |
| 5,106,362 A | 4/1992 | Gilman | |
| 5,113,871 A | 5/1992 | Viljanto et al. | |
| 5,149,331 A | 9/1992 | Ferdman et al. | |
| 5,228,431 A | 7/1993 | Giarretto | |
| 5,261,893 A | 11/1993 | Zamierowski | |
| 5,462,514 A | 10/1995 | Harris | |
| 5,489,280 A * | 2/1996 | Russell | 604/311 |
| 5,549,584 A | 8/1996 | Gross | |
| 5,618,556 A | 4/1997 | Johns et al. | |
| 5,636,643 A | 6/1997 | Argenta | |
| 5,645,081 A | 7/1997 | Argenta | |
| 5,701,917 A | 12/1997 | Khouri | |
| 5,716,411 A | 2/1998 | Orgill et al. | |
| 5,827,246 A | 10/1998 | Bowen | |
| 5,830,496 A | 11/1998 | Freeman | |
| 5,893,368 A | 4/1999 | Sugerman | |
| 5,938,626 A | 8/1999 | Sugerman | |
| 5,970,266 A | 10/1999 | Argenta | |
| 6,045,541 A | 4/2000 | Matsumoto | |
| 6,135,116 A | 10/2000 | Vogel et al. | |
| D434,150 S | 11/2000 | Tumey | |
| 6,142,982 A | 11/2000 | Hunt | |
| 6,176,307 B1 | 1/2001 | Danos et al. | |
| 6,287,521 B1 * | 9/2001 | Quay et al. | 422/101 |
| 6,402,724 B1 | 6/2002 | Smith et al. | |
| 6,458,109 B1 | 10/2002 | Henley et al. | |
| 6,471,685 B1 | 10/2002 | Johnson | |
| 6,595,949 B1 | 7/2003 | Shapiro | |
| 6,695,823 B1 | 2/2004 | Lina et al. | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 6,988,423 B2 | 1/2006 | Bolam et al. | |
| 6,994,702 B1 | 2/2006 | Johnson | |
| 7,004,915 B2 | 2/2006 | Boynton et al. | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,869 B2 | 10/2006 | Heaton et al. | |
| 7,128,735 B2 | 10/2006 | Weston | |

| | | | |
|---|---|---|---|
| 7,198,046 | B1 | 4/2007 | Argenta et al. |
| 7,216,651 | B2 | 5/2007 | Argenta et al. |
| 2001/0029956 | A1 | 10/2001 | Argenta et al. |
| 2002/0065494 | A1 | 5/2002 | Lockwood et al. |
| 2002/0068913 | A1 | 6/2002 | Fleischmann |
| 2002/0115952 | A1 | 8/2002 | Johnson |
| 2002/0143286 | A1 | 10/2002 | Tumey |
| 2002/0161346 | A1 | 10/2002 | Lockwood et al. |
| 2002/0183702 | A1 | 12/2002 | Henley et al. |
| 2002/0198503 | A1 | 12/2002 | Risk |
| 2002/0198504 | A1 | 12/2002 | Risk |
| 2003/0014025 | A1 | 1/2003 | Allen et al. |
| 2003/0040687 | A1 | 2/2003 | Boynton et al. |
| 2003/0050594 | A1 | 3/2003 | Zamierowski |
| 2003/0108587 | A1 | 6/2003 | Orgill et al. |
| 2003/0125646 | A1 | 7/2003 | Whitlock |
| 2004/0054338 | A1 | 3/2004 | Bybordi et al. |
| 2004/0073151 | A1 | 4/2004 | Weston |
| 2004/0127863 | A1 | 7/2004 | Bubb et al. |
| 2005/0148913 | A1 | 7/2005 | Weston |
| 2005/0203452 | A1 | 9/2005 | Weston |
| 2005/0222527 | A1 | 10/2005 | Miller et al. |
| 2005/0222528 | A1 | 10/2005 | Weston |
| 2005/0222544 | A1 | 10/2005 | Weston |
| 2005/0261615 | A1 | 11/2005 | Weston |
| 2005/0261642 | A1 | 11/2005 | Weston |
| 2005/0261643 | A1 | 11/2005 | Bybordi et al. |
| 2007/0239139 | A1 | 10/2007 | Weston et al. |

FOREIGN PATENT DOCUMENTS

| | | |
|---|---|---|
| CA | 2369000 A1 | 10/1990 |
| CA | 2103033 C | 11/1992 |
| CA | 2414393 A1 | 11/1992 |
| CA | 2121688 C | 5/1993 |
| CA | 2115951 A1 | 8/1994 |
| CA | 2157772 C | 9/1995 |
| CA | 2198243 A1 | 2/1996 |
| CA | 2237606 A1 | 5/1997 |
| CA | 2238413 A1 | 5/1997 |
| CA | 2551340 A1 | 5/1997 |
| CA | 2272399 A1 | 11/1997 |
| CA | 2280817 A1 | 2/1998 |
| CA | 2267312 A1 | 4/1998 |
| CA | 2272372 A1 | 5/1998 |
| CA | 2303085 A1 | 3/1999 |
| CA | 2471780 A1 | 3/1999 |
| CA | 2347115 A1 | 4/2000 |
| CA | 2367460 A1 | 10/2000 |
| CA | 2369022 C | 10/2000 |
| CA | 2369024 A1 | 10/2000 |
| CA | 2390513 A1 | 5/2001 |
| CA | 2408305 A1 | 11/2001 |
| CA | 2351342 A1 | 6/2002 |
| CA | 2442724 A1 | 10/2002 |
| CA | 2432293 A1 | 2/2003 |
| CA | 2458285 A1 | 3/2003 |
| CA | 2483654 A1 | 11/2003 |
| CA | 2490027 A1 | 12/2003 |
| CA | 2368085 C | 5/2006 |
| DE | 561757 | 10/1932 |
| DE | 2809828 | 9/1978 |
| DE | 4111122 | 4/1993 |
| GB | 114754 | 4/1918 |
| GB | 641061 | 8/1950 |
| GB | 1273342 | 5/1972 |
| GB | 2195255 A | 4/1988 |
| SU | 240188 | 3/1969 |
| WO | WO 87/04626 | 8/1987 |
| WO | WO 90/11795 | 10/1990 |
| WO | WO 91/00718 | 1/1991 |
| WO | WO 91/16030 | 10/1991 |
| WO | WO 92/19313 | 11/1992 |
| WO | WO 92/20299 | 11/1992 |
| WO | WO 93/09727 | 5/1993 |
| WO | WO 2005/115497 | 12/2005 |

OTHER PUBLICATIONS

Bagautdinov, "Variant of External Vacuum Aspiration in the Treatment of Purulent Diseases of Soft Tissues," Current Problems in Modern Clinical Surgery, 1986, 4 pages.

Boretos, "Cellular Polymers for Medical Use: The Vital Role of Porosity and Permeability," Cellular Polymers, 1984, vol. 3, pp. 345-358.

Chardak et al., "Experimental Studies on Synthetic Substitutes for Skin and Their Use in the Treatment of Burns," Annals of Surgery, 1962, vol. 155, No. 1, pp. 127-139.

Dilmaghani et al., "A Method for Closed Irrigation and Suction Therapy in Deep Wound Infections," Journal of Bone and Joint Surgery, 1969, vol. 51-A, No. 2, pp. 323-342.

International Standard ISO 10079-1, First Edition, May 15, 1991, 2 pages.

Meyer et al., "Bier's Hyperemic Treatment in Surgery, Medicine, and the Specialties: A Manual of Its Practical Application," 1908, 222 pages.

Orringer et al., "Management of Wounds in Patients with Complex Enterocutaneous Fistulas," Surgery, Gynecology, & Obstetrics, Jul. 1987, vol. 165, pp. 79-80.

Robertson, "The Influence upon Wound Contraction of a Negative Interstitial Fluid Pressure Within Granulation Tissue," Journal of Anatomy, 1969, vol. 105, No. 1, pp. 189.

Svedman, "Irrigation Treatment of Leg Ulcers," The Lancet, Sep. 3, 1983, pp. 532-534.

Teder, et al., "Continuous Wound Irrigation in the Pig," Journal of Investigative Surgery, 1990, vol. 3, pp. 399-407.

Tennant, "The Use of Hyperemia in the Postoperative Treatment of Lesions of the Extremities and Thorax," Journal of the American Medical Association, 1915, vol. 64, No. 19, pp. 1548-1549.

Westaby et al., "A Wound Irrigation Device," The Lancet, Sep. 2, 1978, pp. 503-504.

3M Health Care, Controlling the Risk of Surgical Site Infections after Cardiovascular Procedures: The Importance of Providing a Sterile Surface, *Brochure*, St. Paul, MN and London, Ontario, Canada, 1997, 8 pages.

AEROS, "Moblvac II," 1 page.

AEROS, Aeros Instruments, Inc. 1111 Lakeside Dr., Gurnee, IL 60031. Aug. 1993. "Care-E-Vac," 2 pages.

AEROS, Aeros Insturments, Inc. 3411 Commercial Ave., Northbrook, IL 60062. Oct. 1988. Part No. 1504-02 7M. "Instavac Aspirator," 1 page.

Agarwala, S., et al., Use of Mini-Vacuum Drains in Small Surgical Wounds, *Plastic and Reconstructive Surgery*, Apr. 1998, 101(5), 1421-1422 (Correspondence).

Agrama, H.M., Functional Longevity of Intraperiotoneal Drains, *Amer. Journ. of Surg.*, Sep. 1976, 132, 418-421.

Alper, J.C., et al., An Effective Dressing for a Large, Draining Abdominal wound, *RN*, Dec. 1988, 24-25.

Alper, J.C., et al., Moist Wound Healing under a Vapor Permeable Membrane, *Journ. of Amer. Acad. of Derm.*, Mar. 1983, 8(3), 347-353.

Arturson, M. Gosta, "The Pathophysiology of Severe Thermal Injury," *JBCR*, 6(2): 129-146 (Mar.-Apr. 1985).

Ashrafov, A.A. and K.G. Ibishov, An Experimental and Clinical Validation for the Use of a Collagen Sponge for Treating the Suppurative-Inflammatory Complications of Wound Healing in Emergency Abdominal Surgery, *PubMed*, Abs. Downloaded from Internet, Apr. 24, 2006, 1 page.

Aubrey, D.A., et al., Treatment of the Perineal Wound after Proctectomy by Intermittent Irrigation, *Arch. Surg.*, Oct. 1984, 119, 1141-1144.

A Sensational Medical discovery, *Brit. Journ. Nurs.*, Jul. 15, 1911, 42.

Article Excerpt, *Lancet*, Jun. 14, 1952, 1175-1176.

Article Excerpt: Part III. Resolving Selected Clinical Dilemmas, 17-20.

Assessing the Patient with a Fistula or Draining Wounds, *Nursing*, Jun. 1980, 49-51.

Chart: Influence of Wound Closure on Healing of Perineal Wound after Abdominoperineal Resection or Total Proctocolectomy, excerpt faxed Jan. 23, 2006, 1 page.

Hanbok för Hälso-Och Sjukvårdsarbete Lokal Anvisning för Landstinget Sörmland, Jan. 2001, (in Swedish), Downloaded from Internet http://www.landstinget.sormland.se, Aug. 14, 2001, 7 pages.

Hyperemia by Suction Apparatus, *Chapter VIII*, 74-85.

Reference Handbook of the Medical Sciences, *Hyperaemia*, 553.

Specific Inflammations, Diseases of the Skin, 549-550.

The Bier Treatment, *Brit. Journ. Nurs.*, Jun. 6, 1908, 452.

Leherman, "The Not-So-Bald-Truth," *Science*, Sep. 1992, p. 42.

The British Journal of Nursing, Nov. 4, 1911, 368.

Tuberculous Joints, *Nursing record & Hospital World*, Apr. 28, 1894, 280.

Wound Suction: Better Drainage with Fewer Problems, *Nursing* Oct. 1975, 52-53.

Medela, Inc. Product Information (with English Summary): "Pleupump MK II is the new micro-data controlled thoracic drainage," 12 pages.

Avocat, C. et al., Nouvelle Presentation de Materiel Pour Drainage de Redon et Jost, *La Nouvelle Press Medicale*, Jun. 26, 1976, 5(6), 1644-1645 (in French).

Ayoub, M.H. and G. C. Bennet, A Study of Cutaneous and Intracompartmental Limb Pressures Associated with the Combined Use of Tourniquets and Plaster Casts, Abs., *Proc. and Reports of Univ., Colleges, Councils, Assoc., and Societies*, 68-B:3, May 1986, 497.

Baldwin, J.F., Ed., The Columbus Medical Journal, Columbus, Ohio, 1887, vol. 5, 561.

Barbul, A., et al., Eds., Clinical and Experimental Approaches to Dermal and Epidermal Repair, Normal and Chronic Wounds, Progress in Clin. and Biol. Res., vol. 365, *Proc. of the 3rd Intnl. Symp. on Tissue Repair*, Miami, FL, Jan. 10-14, 1990, Abs.

Bar-El, Y. et al., Potentially dangerous Negative Intrapleural pressures Generated by Ordinary Pleural Drainage Systems, *Chest*, Feb. 2001, 119(2), 511-514.

Barker, D.E., et al., Vacuum Pack Technique of Temporary Abdominal Closure: A 7-Year Experience with 112 Patients, *Journ. of Trauma: Injury and Critical Care*, Feb. 2000, 4892), 201-207.

Bascom, J., Pilonidal Sinus, *Current Therapy in Colon and Rectal Surgery*, 1990, 1-8.

Benjamin, P.J., Faeculent Peritonitis: A Complication of Vacuum Drainage, *Br. J. Surg.*, 1980, 67, 453-454.

Berman and Fabiano, Closed Suction Drainage, *Orthopedics*, Mar. 1990, 13(3), 310-314.

Berman, A. T., et al., Comparison Between Intermittent (Spring-Loaded) and Continuous Closed Suction Drainage of Orthopedic Wounds: A Controlled Clinical Trial, *Orthopedics*, Mar. 1990, 13(3), 9 pgs.

Besst, J.A., Wound Healing—Intraoperative Factors, *Nursing Clinics of North America*, Dec. 1979, 14(4), 701-712.

Biblehimer, "Dealing With a Wound that Drains 1.5 Liters a Day," RN, Aug. 1986, pp. 21-23, USA.

Bier, A., Hyperemia as a Therapeutic Agent, Ed. Dr. Gustavus M. Blech, A. Robertson & Co., Chicago 1905, (the entire reference has been submitted, but pp. 74-85 may be the most relevant).

Birdsell, D.C., et al., The Theoretically Ideal Donor Site Dressing, *Gadgetry, Div. of Plastic Surgery, Foothills, Hospital*, Calgary, Canada, 535-537.

Bischoff, et al., Vacuum-Sealing Fixation of Mesh Grafts, *Euro. Journ. Plast. Surg.*, Jul. 2003, 26(4), 189-190, Abs. Downloaded from internet Apr. 6, 2006.

Bonnema, J., et al., A Prospective Randomized Trial of High Versus Low Vacuum Drainage after Axillary Dissection for Breast Cancer, *Amer. Journ. Surg.*, Feb. 1997, 173, 76-79.

Britton, B.J., et al, A Comparison Between Disposable and Non-Disposable Suction Drainage Units: A Report of a Controlled Trial, *Br. J. Surg.* 1979, 66, 279-280.

Broader, J.H., et al., Management of the Pelvic Space after Proctectomy, *Br. J. Surg.*, 1974, 62, 94-97.

Bruno, P., The Nature of Wound Healing: Implications for Nursing Practice, *Nursing Clinics of North American*, Dec. 1979, 14(4), 667-682.

Bucalo et al. "Inhibition of Cell Proliferation by Chronic Wound Fluid." Wound Repair and Regeneration. Miami, 1993. pp. 181-186.

Burdette-Taylor, S.R., Use of the Versatile One (V1) for Closed Suction Drainage to Stimulate Closure in Chronic Wounds in Home Care, Case Study Presentation, 2003, 2 pgs.

Bush, G.K., What is a Counter Irritant? Name Any That You Know and the Method of their Application, *Brit. Journ. Nurs.*, Oct. 1927, 232.

Calhoun, P. and K. Kenney, Pouching Management of Patients with Open abdomen, Eviscerations and Bowel Fistulas, Case Studies, *Univ. of Miami/Jackson Memorial Medical Center*, 1 page.

Candiani, P., et al., Repair of a Recurrent Urethrovaginal Fistula with an Island Bulbocavernous Musculocutaneous Flap, *Plastic and Reconstructive Surgery*, Dec. 1993, 1393-1394.

Carroll, P.L., The Principles of Vacuum and its Use in the Hospital Environment, 2nd Ed., 1986, 30p.

Chariker, M.E., et al, "Effective Management of Incisional and Cutaneous Fistulae with Closed Suction Wound Drainage," Contemporary Surgery, Jun. 1989, pp. 59-63, vol. 34 USA.

Chua Patel, C.T., et al., Vacuum-Assisted Closure, *AJN*, Dec. 2000, 100(12), 45-49.

Clark, R.A.F., The Molecular and Cellular Biology of Wound Repair, Chapter 1: Overview and General Considerations of Wound Repair 1988, 3-33.

Cobb, J.P., Why Use Drains?, *Br. J. Bone Joint Surg.*, Nov. 1990, 72-B(6), 993-995.

Cooper, D.M., Optimizing Wound Healing, *Nursing Clinics of North America*, Mar. 1990, 25(1), 163-179.

Cooper, D.M., Postsurgical Nursing Intervention as an Adjunct to Wound Healing, *Nursing Clinics of North America*, Dec. 1979, 14(4), 713-726.

Cooper, S.M. and E. Young, Topical Negative Pressure, *Commentary, International Journal of Dermatology 2000*, 39, 892-898.

Costunchenok, B.M., et al., Effect of Vacuum on Surgical Purulent Wounds, *Vestnik Chirurgia 1986*, Sep. 18-20 (in Russian with English translation).

Cotton, P.B., et al., Early Endoscopy of Oesophagus, Stomach, and Duodenal Bulb in patients with Haematemesis and Melaena, *Br. Med. Journ.*, Jun. 1973, 2, 505-509.

Crisp, W.J. and A. Gunn, Granuflex Dressings for Closed Surgical Wounds Combined with Suction Drainage, *Annals of the Royal College of Surgeons of England*, 1990, 72, p. 76.

Cucuroos, Y.C., Vacuum Drainage of Post Operative Wounds, *Kiev Army Hospital, Dept. of Hospital Surgery, Kiev Medical University*, 64-65 (in Russian with English translation).

Curtin, L.L., Wound Management: Care and Cost—An Overview, *Nursing Management*, Feb. 1984, vol. 15, 22-25.

Davis, J.C. and T.K. Hunt, Eds., Problem Wounds: The Role of Oxygen, Chap. 1, Infection and Oxygen, 1988, 1-15.

Davidov Y., "Vacuum therapy in the treatment of purulent lactation mastitis," Vestnik Khirurgii, Sep. 1986, pp. 66-70.

Davidov, Y., "Bacteriological and cytological evaluation of the vacuum therapy of suppurative wounds," Vestnik Khirurgii, Oct. 1988, pp. 48-52.

Davidov, Y.A., et al. Justifying the Usage of Force Early Secondary Sutures in treatment of Purulent Wounds by the Vacuum Therapy, *Vestnik Chirurgia 1990*, March Edition, 126-129 (in Russian with English translation).

Davidov, Y.A., et al., Concept of Clinico-Biological Management of Wound Process in Treatment of Purulent Wounds with the Help of Vacuum Therapy, *Vestnik Chirurgia 1991, February Edition*, 132-135 (in Russian with English translation).

Davidov et al. "Pathogenic Mechanism of the Effect of Vacuum Therapy on the Course of the Wound Process" pp. 43-46 (Dec. 1990).

Deknatel, Div. of Howmedica, Inc. Queens Village, NY 11429. "Pleur-evac," 1 page.

Dillon, Angiology, The Journal of Vascular Diseases, "Treatment of Resistant Venous Stasis Ulcers and Dermatitis with the End-Diastolic Pneumatic Compression Boot," Jan. 1986, pp. 47-55.

Doillon, C.J., et al., Collagen-Based Wound Dressings: Control of the Pore Structure and Morphology, Journal of Biomedical Materials Research, Sep. 13, 2004, 20(8), 1219-1228. Abs. Downloaded from Internet http://www3.interscience.wiley.com, Apr. 28, 2006.

Domkowski, P.W., et al., Evaluation of Vacuum-Assisted Closure in the Treatment of Poststernotomy Mediastinitis, *Journ. of Thorac. and Cardiovascular Surg.*, Aug. 2003, 126(2), 386-390.

Doss, Mirko, et al., Vacuum-Assisted Suction Drainage Versus Conventional Treatment in the Management of Poststernotomy Osteomyelitis, *Euro. Journ. Cardio-Thoracic. Surg.* 22 (2002) 934-938.

Draper, J., Make the Dressing Fit the Wound, *Nursing Times*, Oct. 9, 1985, 32-35.

Dunbar, J.M., State What You Have Learned Recently on the Up-to-Date Care of Wounds, *The British Journal of Nursing*, Dec. 1941, 200.

Dunlop, M.G, et al. Vacuum Drainage of Groin Wounds after Vascular Surgery: A Controlled Trial, *Br. J. Surg.*, May 1990, 77, 562-563.

Eaglstein, W.H., et al., Wound Dressings: Current and Future, *Clin. and Exper. Approaches to Dermal and Epidermal Repair: Normal and Chronic Wounds*, 1991, 257-265.

ECRI, Target Report, Negative Pressure Wound Therapy for Chronic Wounds, Jan. 24, 2006, 1-7, Downloaded from internet, http://www.target.ecri.org/summary/detail.aspx?dox_id=1155.

Eisenbud, D.E., Modern Wound Management, *Anadem Publishing*, Chap. 16, 109-116.

Ellingwood, F., Ellingwood's Therapeutist, Jun. 14, 1908, vol. 2(6), 32-33.

Elwood, E.T., and D.G. Bolitho, Negative-Pressure Dressings in the Treatment of Hidradenitis Suppurative, *Annals of Plastic Surgery*, Jan. 2001, 46(1), 49-51.

Emerson, Series 55, J.H. Emerson Co., 22 Cottage Park Ave., Cambridge, MA 02140. "Emerson Post-Operative Suction Pumps," 2 pages.

Engdahl, O. and J. Boe, Quantification of Aspirated Air Volume reduces Treatment Time in Pneumothorax, *Eur. Respir. J.*, 1990, 3, 649-652.

Engdahl, O., et al., Treatment of Pneumothorax: Application of a Technique which Quantifies Air Flow Through the Chest Drain, *Adv. in Therapy*, May/Jun. 1988, 5(3), 47-54.

Erichsen, J.E., Science and Art of Surgery, *London: Longmans, Green, and Co.*, 1895, vol. 1, 258-259, and p. 289.

Fabian, T.S., The Evaluation of Subatmospheric Pressure and Hyperbaric Oxygen in Ischemic Full-Thickness Wound Healing, *Ischemic Full-Thickness Wound Healing*, Dec. 2000, 66(12), 1136-1143.

Falanga, Vincent, "Growth Factors and Chronic Wounds: The need to Understand the Microenvironment." *Journal of Dermatology*, vol. 19: 667-672, 1992.

Fay, M.F., Drainage Systems: Their Role in Wound Healing, *AORN Journal*, Sep. 1987, 46(3), 442-455.

Fellin, R., Managing Decubitus Ulcers, *Nursing Management*, Feb. 1984, 29-30.

Fingerhut, A., et al., Passive vs. Closed Suction drainage after Perineal Wound Closure Following Abdominoperineal Rectal Excision for Carcinoma, *Dis Colon Rectum*, Sep. 1995, 926-932.

Firlit, C.F. and J.R. Canning, Surgical Wound Drainage: A Simple Device for Collection, *Journ. of Urology*, Aug. 1972, 108, p. 37.

Fisher, Jack, and R. W. Bert, Jr., A Technique for Skin Grafting Around Abdominal Wall Fistulas, *Annals of Plastic Surgery*, 11:6, Dec. 1983, 563-564.

Flanagan, et al., Optional Sump: Novel Use of Triple Lumen Closed Drainage System, *Anz. J. Surg.*, Nov. 2002, 72(11), 806-807, Abs. Downloaded from internet Nov. 30, 2003, 1 page.

Fleck, C.A., When Negative is Positive: A Review of Negative Pressure Wound therapy, *Wound Care*, Mar./Apr. 2004, 20-25.

Fleischmann, W. Acta Orthopaedical Belgica, "Treatment of Bone and Soft Tissue Defects in Infected Nonunion," vol. 58, *Suppl. I-1992*, pp. 227-235.

Fleischmann, W. Unfall Chirurg, Springer-Variag, "Vakuumversiegelung zur Behandlung des Weichteilschadens bei offenen Frakturen," (English abstract, no English translation), 1993, pp. 488-492.

Fleischmann, W. Wund Forum Spezial, "Vakuumversiegelung zur Behandlung von Problemwunden" (with English translation: Vacuum Sealing for Treatment of Problematical Wounds), *IHW '94*, 6 pages.

Fleischmann, "Vacuum sealing: indication, technique, and results," *European Journal of Orthopaedic Surgery & Traumatology*, vol. 5(1), 1995, pp. 37-40.

Flynn, M.E. and D.T. Rovee, Wound Healing Mechanisms, *Amer. Journ. of Nursing*, Oct. 1982, 1544-1556.

Fox, J.W. and G.T. Golden, The Use of Drains in Subcutaneous Surgical Procedures, *Amer. Journ. of Surg*, Nov. 1976, 132, 673-674.

Garcia-Rinaldi, R., et al., Improving the Efficiency of Wound Drainage Catheters, Amer. Journ. of Surg., Sep. 1975, pp. 130, 372-373.

Geiger Jones, E., et al., Management of an Iliostomy and Mucous Fistula Located in a Dehisced Wound in a Patient with Morbid Obesity, *J. WOCN*, Nov. 2003, 30(6), 351-356.

Gill, P., What is a Counter-Irritant? Name Three and the Method of Applying them, *Brit. Journ. Nurs.*, Jun. 1934, 142.

Goddard, L., Inflammation: Its Cause and Treatment, *The British Journal of Nursing*, Jan. 1944, 2.

Gogia, Prem P., "The Biology of Wound Healing." *Ostomy/Wound Management.* Nov.-Dec. 1992, pp. 12-20.

Gomco Suction Equipment & Accessories Guide, Catalog, Apr. 2006, 20 pages.

Gouttefangeas, C. et al., Functional T Lymphocytes Infiltrate Implanted Polyvinyl Alcohol Foams During Surgical Wound Closure Therapy, *Clin. Exp. Immunol. 2001*, 124, 398-405.

Grabowski, S., Leczenie ran z zastosowaniem posicśnienia (wg Redona I Josta), *II Klinik Xhieuefxnej AM w Warszawie; klerownik*: Prof. Dr. Z. Lapinski, No. 1, 19-21 (*in Polish*).

Grishdevich, V. and N. Ostrovsky, Postburn Facial Resurfacing with a Split Ascending Neck Flap, *Plastic and Reconstructive Surgery*, Dec. 1993, 1384-1391.

Grobmyer, et al., High-Pressure Gradients Generated by Closed-Suction Surgical Drainage Systems, *Surg. Infect. (Larchmt)*, *Autumn 2002*, 3(3), 245-249, Abs., Downloaded Nov. 30, 2003.

Grover, R. and R. Sanders, Recent Advances: Plastic Surgery, Clinical Review, *BMJ*, Aug. 8, 1998, 317, 397-400.

Gupta, S., Ed., Guidelines for Managing pressure Ulcers with Negative Pressure Wound Therapy, *Advances in Skin & Wound Care Suppl.*, Nov./Dec. 2004, 17(2), 1-16.

Gupta, S., Guidelines for Managing: Pressure Ulcers with Negative Pressure Wound Therapy, Downloaded from internet http://proquest.umi.com on Feb. 3, 2006, 19 pages.

Gwan-Nulla, D.N. and R.S. Casal, Toxic Shock Syndrome Associated with the Use of the Vacuum-Assisted Closure Device, *Ann. Plast. Surg.*, Nov. 2001, 47(5), 552-554.

Hallstrom, B.R. and J.F. Steele, Postoperative Course after Total Hip Arthroplasty: Wound Drainage versus No Drainage, *Orthopaedic Review*, Jul. 1992, 847-851.

Hargens et al., "Control of Circulatory Functions in Altered Gravitational Fields," *Space Physiology Laboratory, Life Science Division, NASA Ames Research Center*, 4 pages.

Hargens et al., "Lower Body Negative Pressure to Provide Load Bearing in Space," *Aviation, Space and Environmental medicine*, Oct. 1991, pp. 934-937.

Harkiss, K., Cheaper in the Long Run, *Community Outlook*, Aug. 1985, 19-22.

Harle, A. Z. Orthop.,"Schwachstellen herkommlicher Drainagen," 127(1989): 513-517.

Hartz, R.S., et al., Healing of the Perineal Wound, *Arch. Surg.*, Apr. 1980, 115, 471-474.

Harvard Pilgrim Health Care, Technology Assessment Policy, TA 6.29 Negative Pressure Wound therapy for Wound Healing, Dec. 2004, pp. 1-6.

Hay, J., et al., Management of the Pelvic Space With or Without Omentoplasty after Abdominoperineal Resection for Carcinoma of the Rectum: a Prospective Multicenter Study, *Eur. J. Surg*, 1997, Abs., 1 page.

Higgins, S., The Effectiveness of Vacuum Assisted Closure (VAC) in Wound Healing, *Centre for Clinical Effectiveness, Monash Medical Centre*, Clayton VIC Australia, Dec. 2003, 1-16.

Hilsabeck, J.R., The Presacral Space as a Collector of Fluid Accumulations Following Rectal Anastomosis: Tolerance of Rectal Anastomosis to Closed Suction Pelvic Drainage, *Amer. Soc. of Colon and Rectal Surgeons*, Oct., 25(7), 680-684.

Hilton, P., Wound Drainage: A Survey of Practices among Gynaecologists in the British Isles, *Br. Journ. of Obstetrics and Gynaecology*, Oct. 1988, 95, 1063-1069.

Hollis, H.W. and M.R. Troy, A Practical Approach to Wound care in patients with Complex Enterocutaneous Fistulas, *Surg., Gyn. & Obs.*, Aug. 1985, 161, 179-181.

Hugh, T.B., Abdominal Wound Drainage, *Med. Journ. of Australia*, May 4, 1987, 146, p. 505 (Correspondence).

Hulten, L., et al., Primary Closure of Perineal Wound after Proctocolectomy or Rectal Excision, *Acta Chir. Scand.*, 1971, 137, 467-469.

Hunt, T.K. and J.E. Dunphy, Eds., Fundamentals of Wound Management, *Appleton-Century-Crofts/New York*, 416-447.

Ilizarov, G.A., The Tension-Stress Effect on the Genesis and Growth of Tissues: Part II., *Clinical Orthopaedics and Related Research*, Feb. 1989, 239, 263-283.

Creative Medical Laboratories, Instruction Manual, Inc. P.O. Box 6347, Rochester, Minn. 55903. "TUGS" (Transportable Universal Gradient Suction), 8 pages.

Izmailov, S.G., et al., Device for Treatment of wounds and Abdominal Cavity, Contents, Downloaded from internet http://www.mediasphera.ru/surgery/97/8/e8-97ref.htm, *Surgery* No. 8 1997, 1 page.

Izmailov, S.G., The Treatment of Eventrations with a Special Apparatus, Abstracts, Downloaded from internet, http://www.mediasphera.ru/surgery/97/1/el-97ref.htm, *Surgery* No. 1 1997, 1 page.

Jeter, K., Closed Suction Wound Drainage System, *J. WOCN*, Mar./Apr. 2004, 51 (correspondence).

Jeter, Katheerine F. ET, "Managing Draining Wounds and Fistulae: New and Established Methods," *Chronic Wound Care*, Chapter 27, pp. 240-246.

Johnson, F.E., An Improved Technique for Skin Graft Placement using a Suction Drain, *Surgery, Gynecology & Obstetrics*, Dec. 1984, 159(6), 584-585.

Kazan Medical Institute Doctors, A Gadget to Bring the Wound Edges Close, 78-79 (in Russian with English translation). Aug. 20, 1985, 4 pages.

KCI, Inc., If It's Not V.A.C. Therapy, It's Not Negative Pressure Wound Therapy, *KCI Brochure*, Jan. 2005, 1-5.

KCI, Inc., Introducing the V.A.C. GranuFoam Silver Dressing, *Flyer*, 2 pages.

KCI, Inc., The V.A.C. System, 2000-2001, Brochure, 2 pages.

KCI, Inc., Vacuum Assisted Closure (VAC) from Wound Healing, *Evidence Note 5, NHS Quality Improvement Scotland*, Nov. 2003, 1 page.

Keen, W.W., Ed., Surgery, Its Principles and Practice, 1919, W. B. Saunders Company, excerpt, p. 56.

Keith, C.F., Wound management Following Head and Neck Surgery, *Nursing Clinics of North America*, Dec. 1979, 14(4) 761-779.

Kennard, H.W., Bier's Hyperaemia, *Brit. Journ. Nurs.*, Mar. 20, 1909, 223.

Khil'Kin, A.M., Use of a Collagen Hemostatic Sponge for the Experimental Closing of the Surface of a Liver Wound (article in Russian), Citation Downloaded from internet http://www.ncbi.nlm.nih.gov Apr. 24, 2006, 1 page.

Kiemele, L.J., et al., Catheter-Based Negative Pressure Wound Therapy: A New Paradigm of Care, *Nursing Home Wound Care consultative Service, Mayo Clinic*, Rochester, MN, 2 pages.

Kim, S.H., et al., Wangensteen Suction Drainage, apparatus in Neurosurgical Practice, *Dept. of Neurosurgery, Yonsei University of College of Medicine*, Seoul, Korea, 1975, 159-160, Abs. (in Korean and Abstract in English).

Kloth, L.C. and J.M. McCulloch, Wound Healing Alternatives in Management, 3rd Ed., Chap. 10, 339-352.

Kordasiewicz, L.M., Abdominal Wound with a Fistula and Large Amount of Drainage Status after Incarcerate Hernia Repair, *J. WOCN*, May/Jun. 2004, 31(3), 150-153.

Kremlin Papers, A Collection of Published Studies Complementing the Research and Innovation of Wound Care, from *Vestnik Khirurgii*, BlueSky Publishing, A Div. of BlueSky Medical Group Inc., 2004, 17 pages.

Landes, R.R. and I. Melnick, An Improved Suction Device for Draining Wounds, *Arch. Surg.*, May 1972, 104, p. 707.

Landis, E.M. and J.H. Gibbon, Jr., The Effects of Alternate Suction and Pressure on Blood Flow to the Lower Extremities, Alternate Suction and Pressure, pp. 925-961.

Larichev, A.B., Vacuum Therapy of Wounds and Wound Infection, *1st. Ed., BlueSky Publishing*, 2005, 237 pgs.

Lee, J.H. and H.J. Yang, Application of Medifoam B® & Negative Pressure Therapy for the Auxiliary Treatment of Pressure Sore, *Dept. Plastic and Reconstructive Surg., College of Medicine, Eulji Univ.*, Daejeon, Korea, Abs. Sep. 31, 2004, 1 page.

Letsou et al. "Stimulation of Adenylate Cyclase Activity in Cultured Endothelial Cells Subjected to Cyclic Stretch." *Cardiovascular Surgery 3*. Toronto. Sep. 1989, pp. 634-639.

Linden van der, Willem, "Randomized Trial of Drainage After Cholecystectomy," *Modern Operative Techniques*, Voluje 141, Feb. 1981, pp. 289-294.

Lockwood, C.B., Aseptic Surgery, Drainage, *Brit. Journ. Nurs.*, Mar. 26, 1904, 245.

Luchette, F.A., When Should the General Surgeon Leave the Abdomen Open?, Division of Trauma, Surgical Critical Care and Burns, Loyola University Medical Center, Maywood, Illinois., 37 pages.

Lumley, J.S.P., et al., The Physical and bacteriological Properties of Disposable and Non-Disposable Suction Drainage Units in the Laboratory, *Br. J. Surg.*, 1974, 61, 832-837.

Lundvall, J. and T. Lanne, Transmission of Externally applied Negative pressure to the Underlying Tissue: A Study on the Upper Arm of Man, *Acta Physiol. Scand. 1989*, 136, 403-409.

Maddin et al., International Journal of Dermatology, "The Biological Effects of a Pulsed Electrostatic Field with Specific References to Hair: Electrotrichogenesis," vol. 29: 446-450 (1990).

Magee, C., et al., Potentiation of Wound Infection by Surgical Drains, *Amer. Journ. of Surg.*, May 1976, 131, 547-549.

Maitland and Mathieson, Suction Drainage, *Brit. J. Surg*, Mar. 1970, 57(3), 195-197.

Mayo, C.W., The One-Stage Combined Abdominoperineal Resection for Carcinoma of the Rectum, RectoSigmoid and Sigmoid, *Surgical Clinics of North America*, Aug. 1939, *Mayo Clinic Number*, 1011-1012.

McFarlane, R.M., The Use of Continuous Suction under Skin Flaps, *Br. Journ. Plast. Surg.*, 77-86.

McGuire, S., Drainage after Abdominal Section, *Br. Journ. of Nurs.*, Dec. 15, 1903, 447-449.

McLaughlan, James, "Sterile Microenvironment for Postoperative Wound Care," *The Lancet*, Sep. 2, 1978, pp. 503-504.

Medela, Inc., Pleupump MK II, Aug. 14, 2001, Brochure (in German), 12 pages.

Mendez-Eastman, S., Guidelines for Using Negative Pressure Wound Therapy, *Advances in Skin & Wound Care*, 14(6), Nov./Dec. 2001, 314-325.

Mendez-Eastman, S., When Wounds Won't Heal, *RN*, Jan. 1998, 2-7.

Meyer and Schmieden, Bier's Hyperemic Treatment, Fig. 69-70, 557.

Meyer and Schmieden, Bier's Hyperemic Treatment, *Published 1908 W. B. Saunders Company*, 44-65.

Meyer, W. & Schmieden, V., *Bier's Hyperemic Treatment, W B. Saunders Company 1908*, (the entire reference has been submitted, but pp. 44-65 may be the most relevant).

Microtek Heritage, Inc. P.O. Box 2487, Columbus, MS 39704, "Wound-Evac ET," 4 pages.

Miles, W.E., A Method of Performing Abdominoperineal Excision for Carcinoma of the Rectum and of the Terminal Portion of the Pelvic Colon, *The Lancet*, Dec. 19, 1908, 1812-1813.

Miller, M.S. and C. McDaniel, Treating a Pilonidal Cystectomy Abscess Wound with the BlueSky Medical Versatile 1™ Negative Pressure Wound Therapy, *The Wound Healing Center*, Terre Haute, Indiana, Case Study 2004-2006, 1 page.

Miller, M.S., Negative Pressure Wound Therapy: "A Rose by Any Other Name," *Ostomy/Wound Management*, Mar. 2005, 51(3), 44-49.

Milsom, I. and A. Gustafsson, An Evaluation of a Post-Operative Vacuum Drainage System, *Curr. Med. Res. Opin.* (1979), 6, 160-164.

Moloney, G.E., Apposition and Drainage of Large Skin Flaps by Suction, *Australian and New Zealand Journ. of Surg.*, 173-179—1950's.

Morykwas, M.J., et al., Effects of Varying Levels of Subatmospheric Pressure on the Rate of Granulation Tissue Formation in Experimental Wounds in Swine, *Abs., Ann. Plast. Surg. 2001*, 47: 547.

Moserova, J. and E. Houskova, The Healing and Treatment of Skin Defects, 1989, 116-143.

Moss, W., What is Cellulitis? Describe Some Forms of Treatment You Would Expect to be Used for Cellulitis of the Arm, *Brit. Journ. Nurs.*, Nov. 1935, 282.

Mulder, G.D., Ed., et al., Clinicians' Pocket Guide to Chronic Wound Repair, *Wound Healing Publications*, Spartanburg, SC, 1991, 54-55.

Mullner, T., et al., The Use of Negative Pressue to Promote the Healing of Tissue Defects: A Clinical Trial Using the Vacuum Sealing Technique, *Br. J. Plast. Surg.*, Apr. 1997, 51(1), 79, Abs.

Musashaikhov, K.T., et al., The Course of Wound Healing under the Influence of Polyphepan in patients with Diabetes Mellitus, Abstracts, Downloaded from internet, http://www.mediasphera.ru/surgery/97/5/e5-97ref.htm, *Surgery* No. 5, 1997,1 page.

Nakayama, Yoshio, et al., A New Method for Dressing of Free Skin Grafts, New Method for Free Skin Grafting, vol. 86, No. 6 Jun. 12, 1989.

Nakayama, Y., et al., "A New Method for the Dressing of Free Skin Grafts", Plastic and Reconstructive Surgery, Dec. 1990 pp. 1216-1219, UK.

Nakayama et al., "A New Dressing Method for Free Skin Grafting in Hands." *Ann. Plast. Surg.*, 26: 499-502 (1991).

Nasser, A.N., The Use of the Mini-Flap Wound Suction Drain in maxillofacial Surgery, *Annals of the Royal College of Surgeons of England*, 1986, 68, 151-153.

Navsaria, P.H., et al., Temporary Closure of Open Abdominal Wounds by the Modified Sandwich-Vacuum Pack Technique, *Br. Journ. Surg.*, 2003, 90, 718-722.

Nghiem, D.D., A Technique of Catheter insertion for Uncomplicated Peritoneal Dialysis, *Surgery, Gynecology & Obstetrics*, Dec. 1983, 157, 575-576.

Nicholas, J. M. Options for Management of the Open Abdomen, Presentation from Emory University School of Medicine, 66 pgs.

Nightingale, K., Making Sense of wound Drainage, *Nursing time* Jul. 5, 1989, 85(27), 40-42.

Noblett, E.A., What is an Empyema? What Operations are Undertaken for its Relief, and What Have You to Say About the After-Nursing?, *Brit. Journ. Nurs.*, Apr. 29, 1916, 375.

O'Byrne, C., Detection and Management of Postoperative Wound Sepsis, *Nursing Clinics of North American*, Dec. 1979, 14(4), 727-741.

Ohotskii, V.P., et al., Usage of Vacuum Suction During the Primary Surgical Debridement of Open Limb Injuries, *Sovetskaya Medicina*, 1973, January, 8 pages (in Russian with English translation).

Olenius et al., "Mitotic Activity in Expanded Human Skin." *Plastic and Reconstructive Surgery*. Feb. 1993. 213-215.

Ontario, Vacuum Assisted Closure Therapy for Wound Care, Dec. 2004, Toronto, ON, Canada, pp. 1-59.

Ontario Ministry of Health and Long Term Care for the Ontario Health Technology Advisory Committee, "Vacuum Assisted Closure Therapy for Wound Care, Health Technology Literature Review," Dec. 2004, Toronto, Ontario, Canada, pp. 1-57.

Orgill, D. P., et al., Microdeformational Wound Therapy—A New Era in Wound Healing, *Tissue Engin. and Wound Healing Laboratory, Brigham and Women's Hospital, Business Briefing: Global Surgery—Future Direction 2005*, 22.

Orgill, D. et al., Current Concepts and Approaches to Wound Healing, *Critical Care Medicine*, Sep. 1988, 16(9), 899-908.

Orgill, D.P., et al., Guidelines for Treatment of Complex Chest Wounds with Negative Pressure Wound Therapy, *Wounds, A Compendium of Clinical Research and Practice, Suppl. B*, Dec. 2004, 1-23.

Oschsner, A.J., Surgical Diagnosis and Treatment, 1921, 11, 266-269.

Parker, M.J. and C. Roberts, Closed suction Surgical Wound Drainage after Orthopaedic Surgery, *Cochran Database of Systematic Review 2005*, 3, 3 pages.

Parulkar, B.G., et al., Dextranomer Dressing in the Treatment of Infected Wounds and Cutaneous Ulcers, *J. Postgrad. Med.*, 1985, 31(1), 28-33.

Penman, M., What Are the Signs and Symptoms of Gallstones? What Instruments Would You have Ready for the Operation? How Would You Nurse a Case After Operation?, *Brit. Journ. Nurs.*, Aug. 9, 1919, 88.

Pham, C., et al., Vacuum-Assisted Closure for the Management of Wounds: An Accelerated Systematic Review, *Asernip-Accelerated Review of Vacuum Assisted Wound Closure*, Report No. 27, Dec. 2003, 1-52.

"Pleur-evac. Adult-Pediatric, Non-Metered." Code No. A-4000. Control No. F7961J, 1 page.

Precision Medical, Power VAC+ Intermittent Aspirator, http://precisionmedical.com Downloaded from internet Apr. 10, 2006, 2 pages.

Ramirez, O.M., et al., Optimal Wound Healing under Op-Site Dressing, Ideas and Innovations, 73(3), pp. 474-475.

Ranson, John H. M.D., Safer Intraperitoneal Sump Drainage, Surgery Gynnecology and Obstetrics, pp. 841-842, 1973 vol. 137.

Rammensee, H.G., Untersuchung der Lymphozytenin filtrate in Implantierte PVA-Schwämme nach der Therapie infizierter Wunden mit Vakuumversiegelung, Aus dem Interfakultären Institut für Zellbiologie der Universität Tübingen Abeilung Immunologie Abteilungsleter, 2004, 119 pgs.

Redon, H. and J. Troques, La Fermeture Sous Depression des Plaies Etendues, *Academie de Chirurgie*, Mar. 1954, 304-306. (in French).

Redon, H., Closure of Large Wounds under a Partial Vacuum, Paris, *Notes on Practical Medicine, published under L. Rouques*, 1-3.

Reedy, J., The Science Behind Wound Healing, *UW Health Sciences/UW Medicine News and Community Relations, Winter/Spring 2005*, 4 pages.

Reimann, D., et al., Successful Treatment Due to Vacuum Seal Technique of a Severe Scedosporium Apiospermum Skin Infection in a Renal Transplant Recipient, *Nephrol. Dial. Transplant*, 2004, 19 (1), 245-248.

Richter, Treatment of Inflammatory Conditions of the Skin with Hot Baths, *Brit. Journ. Nurs.*, Aug. 25, 1906, 149.

Roberts, R.H., et al., Randomised Trial of Medinorm LVS and Surgivac Drainage System after Operations for Breast Cancer May 1999, *Amer. Journ. Surg.*, Feb. 1997, 2 pgs.

Rodrigo, J.J., et al., The Effect of Varying Degrees of Suction Pressure on Drainage of Hematomas, *Dept. of Orthopaedic Surgery, University of California, David*, Sacramento, California, 9 pages.

Rosser, C.J., et al., A New Technique to Manage Perineal Wounds, *Infections in Urology*, Mar./Apr. 2000, 4 pgs.

Royle, G.T. and B.J. Britton, Disposable Drains, *Articles of the Royal College of Surgeons of England*, (1984), vol. 66, 1 page.

Russ and Fleischmann, Vakuumversiegelung, List of References (in English and German), 2000, 4 pgs.

Sagi, A., Burn Hazard from Cupping—An Ancient Universal Medication Still in Practice, *burns*, 1988, 14(4), 323-325.

Sames, C.P., Sealing of Wounds with Vacuum Drainage, *Br. Med. Journ.*, Nov. 5, 1977, p. 1223, Correspondence.

Samson, D., et al., Wound-Healing Technologies: Low-Level Laser and Vacuum-Assisted Closure, *Evidence report/Technology Assessment*, No. 111, Dec. 2004, AHRQ Publication No. 05-E005-2, 97 pages.

Sandahl, L., Slides at Geisinger Medical Center, Danville, PA, Apr. 10, 1990, Correspondence, 4 pages.

Schaffer, D.B., Closed Suction Wound Drainage, Nursing 97, Nov., Downloaded from internet www.springnet.com, 62-64, 1997.

Schumann, D., Preoperative Measures to Promote Wound Healing, *Nursing Clinics of North America*, Dec. 1979, 14(4), 683-699.

Scott, F., Babies in Bottles, *Advance for Resp. Care Practitioners*, Nov. 23, 1992, 2 pgs.

Senyutovich, R.V., Napkin Preventing Abdominal Contamination in Performance of Colonic Anastomosis, Abstracts, Downloaded from internet, http://www.mediasphera.ru/surgery/97/1/el-97ref.htm—1997, 1 page.

Shaer, W.D., et al., Inexpensive Vacuum-Assisted Closure Employing a Conventional Disposable Closed-Suction Drainage System, *Plastic and Reconstructive Surgery*, Jan. 2001, 292.

Sheen, A.W., Some Experiences of Shell Wounds in the Present War, (excerpt), *Brit. Journ. Nurs.*, Jan. 16, 1915, 42.

Smith, L.A., et al., Vacuum Pack Technique of Temporary Abdominal Closure: A Four-Year Experience, *Amer. Surg.*, Dec. 1997, 63(12), 1102-1108.

Sparta Instrument Corp. 26602 Corporate Ave., Hayward, CA 94545, "Power Source Multi-Purpose Surgical Aspirator," 1 page.

Stewart, M. F., et al., Cleaning v Healing, *Community Outlook*, Aug. 1985, 22-26.

Surgidyne, Closed Systems for Management of Wound Drainage, Brochure and Catalog, Downloaded from internet, www.sterion.com, 6 pages.

Svedman, P., "A Dressing Allowing Continuous Treatment of a Biosurface," *IRCS Med. Science: Biomed. Tech.; Clinic. Med.; Surg. and Transplantation*, 1979, 7, p. 221.

Svedman, P., et al., "A Dressing System Providing Fluid Supply and Suction Drainage Used for Continuous or Intermittent irrigation," *Annals of Plastic Surgery*, vol. 17, No. 2, Aug. 1986, pp. 125-133.

Swanson, L., Solving Stubborn-Wound problem Could Save Millions, Team Says, *JAMC, 23 FEVR*, 1999: 160(4), p. 556.

Techno Takatsuki Co., Ltd., 8-16 Hatchonishimachi, Takatsuki City, Osaka, Japan, "HiBlow Air Pump," 5 pages.

Tenta, L.T., et al., Suction Drainage of Wounds of the Head and Neck, *Surg. Gyn. & Ob.*, Dec. 1989, 169, p. 558.

Tittel, K. and G. Tolksdorff, Forum: VariDyne—Neue Standard in der Postoperative Wunddrainage (New Standards in Postoperative Wound Drainage), *Unfallchirurgie*, 1988 14(2), 104-107 (in German with English Translation).

Tribble, David E. M.D., "An Improved Sump Drain-Irrigation Device of Simple Construction," *Archives of Surgery New York*, 1972 vol. 105, pp. 511-513.

Urschel, J.D., et al., The Effect of Mechanical Stress on Soft and Hard Tissue Repair; A Review, *Br. Journ. Plast. Surg.*, 1988, 41, 182-186.

U.S. Appl. No. 11/491,578, filed Jul. 24, 2006, Title: Negative Pressure Protection System.

U.S. Appl. No. 11/654,926, filed Jan. 17, 2007, Title: Container and Cover System.

U.S. Appl. No. 11/784,021, filed Apr. 5, 2007, Title: Instructional Medical Treatment System.

Usypov, Y. N. and M.V. Ephfanov, Active Drainage of wounds, Dept. of Hospital Surgery, Army Medical Academy, Leningrad, *Vestnik Chirurgia 1987*, April Edition, 42-45 (in Russian with English translation), 6 pages.

Valenta, A.L., Using the Vacuum Dressing Alternative for Difficult Wounds, *AIN*, Apr. 1994, 44-45.

Van Heurn, L.W.E. and P.R.G. Brink, Prospective Randomized Trial of High versus Low Vacuum Drainage after Axillary Lymphadenectomy, *Br. Journ. Surg. 1995*, 82, 931-932.

Van Way III, C.W., Prevention of Suction-Induced Gastric mucosal damage in Dogs, *Critical Care Medicine*, Aug. 1987, 15(8), 774-777.

Varley, G.W. and S.A. Milner, Wound Drains in Proximal Femoral Fracture Surgery: A Randomized prospective Trial of 177 Patients, *J. R. Coll. Surg. Edinb.*, Dec. 1995, 40, 416-418.

Vijanto, J. and J. Raekallio, Local Hyperalimentation of Open Wounds, *Br. J. Surg.*, 1976, 63, 427-430.

Wackenfors, A., et al., Effects of Vacuum-Assisted Closure Therapy on Inguinal Wound Edge Microvascular Blood Flow, *Wound Rep. Reg*, 2004, 12, 600-606.

Warren, J.C. and A.P. Gould, Ed., The International Text-Book of Surgery, 1902, 1, 70-79.

Waymck, J.P., et al., An Evaluation of Aquaphor Gauze Dressing in Burned children, Abs., 1 page.

Wayne, M.A., Cook Pneumothorax Catheter Set, Wayne Pneumothorax Catheter Set, *Cook Critical Care, Cook Incorporated 1997*, 3 pgs.

Wells Johnson Company, 2045 N. Forbes Blvd., Suite 106, Tuscon, AZ. "Point 5 Aspirator," 1 page.

Westaby, S., Wound Care No. 11, *Nursing Times*, Jul. 21, 1982, 41-48.

White, R.A., et al., Vacuum-Assisted Closure Complicated by Erosion and Hemorrhage of the Anterior Tibial Artery, *Journal of Orthopaedic Trauma*, Jan. 2005, 19(1), 56-59, Abs. Cited in BlueSky internal email dtd. Nov. 9, 2005.

Williams, et al., Survey of the Use of Suction Drains in head and Neck Surgery and Analysis of Their Biomechanical Properties, *J. Otolaryngol.*, Feb. 2003, 32(1), 16-22, Abs. Downloaded from internet Nov. 30, 2003.

Windows on Medical Technology, Vacuum-Assisted Wound Closure for Chronic and Acute Wounds, *ECRI Health Technology Assessment Information Service*, Oct. 2000, 38, 1-21.

Witkowski, J.A. and Parish, L.C., Synthetic Dressings: Wound Healing in the '80s, *Hospital Therapy*, Nov. 1986, 75-84.

Wooding-Scott, et al, "No Wound is Too Big for Resourceful Nurses," RN, Dec. 1988, pp. 22-25, USA.

Worth, M.H. and H.W. Andersen, The Effectiveness of Bacterial Filtration in Vented Wound Drains, *Journ. of Surg. Research*, 1979, 27, 405-407.

Wu, P., et al., In Vitro Assessment of Water Vapour Transmission of Synthetic Wound Dressings, *Biomaterials*, 1995, 16(3), 171-175.

Wu, W.S., et al. Vacuum therapy as an intermediate phase in wound closure: a clinical experience, *Eur J Past Surg* (2000) 23: 174-177.

Wysocki et al., "Wound Fluid form Chronic Leg Ulcers Contains Elevated Levels of Metalloproteinases MMP-2 and MMP-9." *The Society for Investigative Dermatology, Inc.* Jul. 1993, 64-68.

Yukhtin, V.I., et al., Surgical Treatment of Purulent Diseases of Soft tissues and Bones with the Use of Drainage-Bathing System, Content, Downloaded from internet, http://www.mediasphera.ru/surgery/97/9/e9-97ref.htm, *Surgery* No. 9 1997, 1 page.

Zhetimkarimov, D.S. and V.K. Ostrovsky, The Applied Significance of Anatomic Pecularities of Greater Momentum, Contents, Downloaded from internet http://www.mediasphera.ru/surgery/97/6/e6-97ref.htm, *Surgery* No. 6, 1997, 1 page.

Chariker, M.E., et al, "Effective Management of Incisional and Cutaneous Fistulae with Closed Suction Wound Drainage," Contemporary Surgery. Jun. 1989, pp. 59-63, vol. 34 USA.

Biblehimer, Helen L., "Dealing With a Wound that Drains 1.5 Liters a Day," RN, Aug. 1986, pp. 21-23, USA.

Wooding-Scott, Margaret, et.al, "No Wound is Too Big for Resourceful Nurses," RN, Dec. 1988, pp. 22-25, USA.

Garcia-Renaldi, Raul, et al, "Improving the Eficiency of Wound Drainage Catheters," Journal of Surgery (?), Sep. 1975, pp. 372-373, vol. 130.

Schwab, Peter M. and Kelly, Keith A., "Primary closure of the Perineal Wound After Proctectomy," Mayo Clinic Proc., Mar. 1974, pp. 176-179, vol. 49, USA.

Ramirez, Oscar M., et al, "Optimal Wound Healing Under Op-Site Dressing," pp. 474-475, vol. 73, No. 3.

Raffl, Arthur B., "Use of Negative Pressure Under Skin Flaps After Radical Mastectomy," Dept. of Surgery, State Univ. of N.Y., College of Medicine Syracuse, NY, Submitted for publication Apr. 1953, p. 1048, USA.

Knight, Marie Ray, A Second Skin for Patients with Large Draining Wounds, Nursing, Jan. 1976, p. 37, USA.

Finley, John M.,"Practical Wound Management," pp. 45, 127, 143, 149, 207.

Spengler, Michael D., el al, "Performance of Filtered Sump Wound Drainage Tubes", Surgery, Gynecology & Obstetrics, Mar. 1982, pp. 333-336, vol. 54, USA.

Kohlman, Phyllis A., et al, "Pouching Procedure to Collect Drainage From Around a Biliary Drainage Catheter," Ostomy/Wound Management, Nov./Dec. 1991, pp. 47-50, vol. 37.

Alper, Joseph, C., "Recent Advances in Moist Wound Healing," Southern Medical Journal, Nov. 1988, pp. 1398-1404, vol. 79, No. 11 USA.

Reid, Daniel P., "Information on Cupping or using suction Cups on Wounds for healing purposes", From Chinese Herbal Medicine.

Taylor, Virginia, Meeting the Challenge of Fistulas & Draining Wounds, Nursing, Jun. 1980, pp. 45-51, USA.

"General Characteristics of Wound Healing and Russian Classificaiton of Wound Healing Process,".

Davydov, Yu. A., et al, Article in Russian (?): Abstract in English: "Vacuum Therapy in the Treatment Purulent Lactation Mastitis" pp. 66-70.

Davydov, Yu. A., et al, Article in Russian (?): Abstract in English: "The Bacteriological and Cytological Assessment of Vacuum Therapy of Purulent Wounds", pp. 48-52.

Article 3, Article in Russian (?), 1991, pp. 126-128.

Article 4, Article in Russian (?), 1991, pp. 132-135.

Alexander, J. Wesley, "Prevention of Wound Infections," The American Journal of Surgery, Jul. 1976, pp. 59-63, vol. 132, USA.

Sheppard, M.D., "Sealed Drainage of Wounds", The Lancet, Jun. 14, 1952, pp. 1174-1176.

Putney F. Johnson, "The Use of Continuous Negative Pressure after Laryngectomy and Radical Neck Dissection", Surgery, Gynecology & Obstetrics, Aug. 1956, pp. 244-246, USA.

Brummelkamp, W.H., et al, "High-vacuum drainage and primary perineal wound closure in abdominoperineal excision of the rectum", The Netherlands Journal of Surgery, 1991 pp. 236-238, Netherlands.

Miles, W. Ernest, "Technique of the Radical, Operation for Cancer of the Rectum", The British Journal of Surgey, pp. 292-304, United Kingdom.

Unknown, "Wound Suction", Nursing, Oct. 1975, pp. 52-53, USA.

Brubacher, Lynda L., "To Heal a Draining Wound", RN, Mar. 1982, pp. 30-35, USA.

Betancourt, Sergio, "A Method of Collecting the Effluent from Complicated Fistual of the Small Intestine," Dept. of Surgery, Allegheny General Hospital, Pittsburgh, p. 375, USA.

Wolthuis, Roger A., et al, "Physiological Effects of Locally Applied Reduced Pressure in Man," Physiological Reviews, Jul. 1974, pp. 566-595 vol. 54, No. 3, USA.

Zamierowski, David S., Letter:"All Foam Sponges are not Equal in Vacuum Dressings," British Journal of Plastic Surgery, 1999, 52, 78-81, p. 79, United Kingdom.

Spahn, Slide presented at the WOCN meeting in Ontario, California, Sep. 2001.

Unknown, "The RN Magazine/University of California Continuing Education Curriculum; Examination on 'To heal a draining wound'", RN, Mar. 1982, p. 36, USA.

Unknown, Medela product information in English Summary: "Pieupump MK II is the new micro-data controlled thoracic drainage".

* cited by examiner

REDUCED PRESSURE WOUND CUPPING TREATMENT SYSTEM

CROSS REFERENCES TO OTHER APPLICATIONS

This application claims the benefit of U.S. provisional application No. 60/559,727, filed on Apr. 5, 2004. The full disclosure of this provisional application is incorporated herein by reference.

BACKGROUND

The present invention generally relates to treatment of wounds, and more specifically to improved apparatus and methods for treating a wound on a patient's body by applying reduced pressure to the body at the site of the wound. In this context, the term "wound" is to be interpreted broadly, to include any wound that may be treated using reduced pressure.

The treatment of open or chronic wounds that are too large to spontaneously close or otherwise fail to heal by means of applying reduced pressure to the site of the wound is well known in the art. One such system is disclosed in U.S. patent application Ser. No. 10/652,100, which was filed with the U.S. Patent and Trademark Office on Aug. 28, 2003. The disclosure of this U.S. patent application is incorporated herein by reference. Another system is disclosed in U.S. patent application Ser. No. 11/026,733, entitled "Improved Reduced Pressure Wound Treatment Appliance," which was filed with the U.S. Patent and Trademark Office on Dec. 30, 2004. The disclosure of this U.S. patent application is also incorporated herein by reference. Yet another system is disclosed in U.S. patent application Ser. No. 11/064,813, entitled "Improved Flexible Reduced Pressure Wound Treatment Appliance," which was filed with the U.S. Patent and Trademark Office on Feb. 24, 2005. The disclosure of this U.S. patent application is also incorporated herein by reference.

Reduced pressure wound treatment systems currently known in the art commonly involve placing a treatment device that is impermeable to liquids over the wound, using various means to seal the treatment device to the tissue of the patient surrounding the wound, and connecting a source of reduced pressure (such as a vacuum pump) to the treatment device in a manner so that an area of reduced pressure is created under the treatment device in the area of the wound. The systems also typically act to remove exudate that may be aspirated from the wound. Thus, such systems also typically have a separate collection device located between the reduced pressure source and the treatment device to collect. This collection device represents a separate source of expense in reduced pressure wound treatment. In addition, it is advantageous in some circumstances to remove exudate from the wound so that the exudate does not remain in the presence of the wound. For example, healing of the wound may be enhanced by the removal of exudate from the wound in some circumstances. In yet other cases, it may be advantageous to be able to gain physical access to the wound without having to remove the treatment device from the body surrounding the wound. For example, it may be desirable to monitor or treat the condition of the wound during the treatment process. If the treatment device is sealed to the body using an adhesive tape, removing the adhesive tape to monitor or treat the wound may cause discomfort and pain for the patient.

Therefore, there is a need for a wound treatment device that can eliminate the requirement for a separate collection device to collect exudate from the wound. This type of device could reduce the expense involved in wound treatment by eliminating the need for the collection device. There is also a need for such a treatment device to remove exudate from the presence of the wound to aid in wound healing. It may also be desirable for this type of treatment device to be disposable in certain circumstances. Further, there is a need for a treatment device that would allow for physical access to the wound without the need for removing the treatment device from the body. This type of device could enhance patient comfort. In addition, where the access is simple and quickly obtained, it could also decrease the cost of wound treatment by reducing the time required of healthcare practitioners to be involved in wound treatment. Finally, there is also a need for a reduced pressure treatment system that is relatively inexpensive, while meeting the needs described above.

SUMMARY

The present invention is directed to reduced pressure treatment appliances and methods that satisfy the needs described above. As described in greater detail below, they have many advantages over existing reduced pressure treatment apparatus and methods when used for their intended purpose, as well as novel features that result in new reduced pressure treatment appliances and methods that are not anticipated, rendered obvious, suggested, or even implied by any of the prior art apparatus or methods, either alone or in any combination thereof.

In accordance with the present invention, a treatment appliance is provided for treating a wound on a body by applying reduced pressure (i.e., pressure that is below ambient atmospheric pressure) to the wound in a controlled manner for a selected time period in a manner that overcomes the disadvantages of currently existing apparatus. For example, the application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

In one embodiment of a first version of the present invention, an appliance for treating a wound on a body is comprised of a cover, sealing means to seal the cover to the body, which are described in more detail below, and reduced pressure supply means, which are also described in more detail below. The cover, which is sized to be placed over and enclose the wound, is further comprised of a top cup member, an interface member, and interface attachment means for removably attaching the top cup member to the interface member. The interface member is further comprised of flow control means that permit exudate from the wound to flow from the wound into the top cup member, but not in the opposite direction. Thus, in this embodiment, the interface member is sealed to the body by the sealing means and exudate from the wound flows from the wound through the flow control means in the interface member into the volume of the cover above the interface member. The flow control means do not allow the exudate to flow back into the area of the wound under the interface member. The cover and the sealing means allow reduced pressure to be maintained in the volume under the cover at the site of the wound. The reduced pressure supply means operably connect the cover to a reduced pressure supply source that provides a supply of reduced pressure to the cover, so that the volume under the cover at the site of the wound is supplied with reduced pressure by the reduced pressure supply source.

In some embodiments of this first version of the present invention, the cover may be approximately cylindrical in shape. In other embodiments, the cover may be approximately cup-shaped. In some embodiments, the sealing means may be comprised of the suction of the interface member against the body, such suction being produced by the presence of reduced pressure in the volume under the cover at the site of the wound. In still other embodiments, the top cup member and the interface member are each comprised of materials from the group consisting of semi-rigid materials, rigid materials, and combinations of such materials. Further, in some embodiments, the interface member is further comprised of a membrane portion that is disposed approximately adjacent to the body and the flow control means is comprised of at least one one-way valve operably disposed in the membrane portion. In other embodiments, the interface member may be further comprised of a membrane portion that is disposed approximately adjacent to the body and that permits fluid to flow in only one direction, and the flow control means is comprised of all or a portion of the membrane. In some embodiments of this first version of the present invention, the interface attachment means may be comprised of an o-ring seal or a magnetic seal. In other embodiments, a portion of the interface member may be of a size and shape adapted to fit tightly against a portion of the top cup member, wherein an operable seal (described in more detail below) is created between the interface member and the top cup member. In yet other embodiments, the sealing means may be comprised of an adhesive that is disposed between a portion of the cover and the portion of the body adjacent to said portion of the cover. In still other embodiments, the sealing means may be comprised of an adhesive tape that is disposed over a portion of the cover and the portion of the body adjacent to said portion of the cover. In other embodiments, the top cup member is further comprised of a port and flow shutoff means operably connected to the port, wherein the flow shutoff means halt or inhibit the supply of reduced pressure to the cover when the level of exudate under the cover at the site of the wound reaches a predetermined level. In yet other embodiments, the interface attachment means does not provide for removal of the top cup member from the interface member.

In some embodiments of this first version of the present invention, the top cup member of the cover may be further comprised of a lid member, a cup body member, and lid attachment means to removably attach the lid member to the cup body member. In some of these embodiments, the cover is approximately cylindrical in shape. In other embodiments, the interface attachment means provides for removable attachment of the top cup member to the interface member, but does not provide for permanent attachment of the top cup member to the interface member. In some of these embodiments, the interface attachment means may be comprised of an o-ring seal or a magnetic seal. In other embodiments, a portion of the interface member may be of a size and shape adapted to fit tightly against a portion of the top cup member, wherein an operable seal is created between the interface member and the top cup member. In still other embodiments, the interface attachment means provides for permanent attachment of the top cup member to the interface member, but does not provide for removable attachment of the top cup member to the interface member. In yet other embodiments, the lid attachment means may be comprised of an o-ring seal or a magnetic seal. In other embodiments, a portion of the lid member is of a size and shape adapted to fit tightly against a portion of the cup body member, wherein an operable seal is created between the lid member and the cup body member.

In other embodiments of this first version of the present invention, the cover is comprised of a lid member, a cup body member, and lid attachment means to removably attach the lid member to the cup body member. In these embodiments, the cover is sized to be placed over and enclose the wound and adapted to maintain reduced pressure in the volume under the cover at the site of the wound. Also in these embodiments, the sealing means, which are described in more detail below, are used to seal the cup body member of the cover to the body so that reduced pressure may be maintained in the volume under the cover at the site of the wound. Reduced pressure supply means operably connect the cover to a reduced pressure supply source, which provides a supply of reduced pressure to the cover so that the volume under the cover at the site of the wound is supplied with reduced pressure by the reduced pressure supply source. In some of these embodiments, the lid attachment means may be comprised of an o-ring seal or a magnetic seal. In other embodiments, a portion of the lid member is of a size and shape adapted to fit tightly against a portion of the cup body member, wherein an operable seal is created between the lid member and the cup body member. In some of these embodiments, a portion of the lid member is approximately cylindrical in shape and a portion of the cup body member is approximately cylindrical in shape and said portions have threads and means to receive threads, so that when such portions are screwed together an operable seal is created between the lid member and the cup body member.

In a second version of the present invention, an appliance for administering reduced pressure treatment to a wound on a body is comprised of a treatment device and a vacuum system. In various embodiments of this second version of the invention, the treatment device is also comprised of a cover and sealing means, which may have substantially the same structure, features, characteristics and operation as the cover and sealing means, respectively, described above in connection with the first version of the present invention. In this second version of the invention, the vacuum system is further comprised of a reduced pressure supply source that provides a supply of reduced pressure and reduced pressure supply means (which are described in more detail below) to operably connect the treatment device to the reduced pressure supply source, so that the volume under the treatment device at the site of the wound is supplied with reduced pressure by the reduced pressure supply source. In various embodiments of this second version of the invention, the reduced pressure supply means may generally have substantially the same structure, features, characteristics and operation as the reduced pressure supply means described above in connection with the first version of the invention.

In some embodiments of this second version of the invention, the reduced pressure supply source is comprised of a vacuum pump. In some of these embodiments, the reduced pressure supply source further comprises a control system for the vacuum pump, wherein the control system may control at least the level of suction produced by the vacuum pump or the rate of fluid flow produced by the vacuum pump, or any combination of rate of suction and rate of fluid flow of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms or fluids (or both) aspirated from the wound. In yet other embodiments, the vacuum pump is comprised of a portable vacuum pump. In still other embodiments of this second version of the invention, the reduced pressure supply means is comprised of flexible tubing. In other embodiments, the cover is further comprised of a port and flow shutoff means, wherein the flow shutoff means halts or inhibits the application of reduced pressure to the cover when exudate from the wound reaches a predetermined level within the cover. In yet other embodiments of this second version of the invention, the reduced pressure under the cover at the site of the wound is in the range from approximately 20 mm of Hg below atmospheric pressure to approximately 125 mm of Hg below atmospheric pressure. In other embodiments, the reduced pressure is applied in a cyclic nature, the cyclic nature providing alternating time periods of application of reduced pressure and without application of reduced pressure.

In a third version of the present invention, an appliance for administering reduced pressure treatment to a wound on a body is comprised of a treatment device and a vacuum system. In various embodiments of this third version of the invention, the treatment device is also comprised of a cover and sealing means, which may have substantially the same structure, features, characteristics and operation as the cover and sealing means, respectively, described above in connection with the first and second versions of the present invention. In the various embodiments of this third version of the invention, the vacuum system is comprised of a suction bulb, which may (but not necessarily) provide a source of reduced pressure, and reduced pressure supply means, which are described in more detail below, to operably connect the cover to the suction bulb, so that the site of the wound in the volume under the cover may be supplied with reduced pressure by the suction bulb. In some embodiments of this third version of the invention, the suction bulb is further comprised of an inlet port and an outlet port, wherein the inlet port is operably connected to the reduced pressure supply means, and the vacuum system further comprises an exhaust tubing member operably connected to the outlet port. In some of these embodiments, the vacuum system further comprises an exhaust control valve operably connected to the exhaust tubing member. In other embodiments, the vacuum system is further comprised of a filter operably connected to the exhaust tubing member, which prevents the venting of micro-organisms or fluids (or both) aspirated from the wound. In yet other embodiments, the vacuum system is further comprised of a supplemental vacuum system that is operably connected to the exhaust tubing member. In these embodiments, the supplemental vacuum system may generally have substantially the same structure, features, characteristics and operation as the vacuum system described above in connection with the second version of the invention.

A fourth version of the present invention discloses a method of treating a wound. In one embodiment of this fourth version of the invention, the method comprises the following steps. First, a cover is positioned on the body over the wound, wherein the cover may have substantially the same structure, features, characteristics and operation as the embodiments of the cover described above in connection with the first, second and third versions of the invention. Second, the cover is operably sealed to the body so that reduced pressure may be maintained in the volume under the cover at the site of the wound. Third, the cover is operably connected with a vacuum system for producing reduced pressure in the volume under the cover at the site of the wound. Fourth, the reduced pressure is maintained until the wound has progressed toward a selected stage of healing. In other embodiments of this fourth version of the invention, the vacuum system is comprised of a suction bulb and the method further comprises the step of squeezing the suction bulb to reduce its volume and then releasing the suction bulb, so that reduced pressure is produced in the volume under the cover at the site of the wound. In other embodiments of this fourth version of the invention, the reduced pressure under the cover at the site of the wound is in the range from approximately 20 mm of Hg below atmospheric pressure to approximately 125 mm of Hg below atmospheric pressure. In still other embodiments of this fifth version of the invention, the reduced pressure is applied in a cyclic nature, the cyclic nature providing alternating time periods of application of reduced pressure and without application of reduced pressure. In other embodiments, the cover is further comprised of a lid member, a cup body member, and lid attachment means to removably attach the lid member to the cup body member, and the method further comprises the steps of halting the application of reduced pressure to the cover, removing the lid member from the cup body member, and attending to the wound. In some of these embodiments, the method further comprises the steps of re-attaching the lid member to the cup body member after attending to the wound and then reapplying reduced pressure to the volume under the cover in the area of the wound. In still other embodiments of this fourth version of the invention, the top cup member further comprises a port and flow shutoff means operably connected to the port, wherein the flow shutoff means halts or hinders the supply of reduced pressure to the volume under the cover in the area of the wound when the level of exudate within the cover reaches a predetermined level. In these embodiments, the method may further comprise the steps of monitoring the level of exudate aspirated from the wound that accumulates within the volume of the cover and removing the cover from the body when the level of exudate aspirated from the wound causes the flow shutoff means to halt or hinder the supply of reduced pressure to the volume under the cover in the area of the wound. It is to be noted that in various other embodiments the steps described above may be performed in a different order than that presented.

The present invention therefore meets the needs discussed above in the Background section. For example, some embodiments of the present invention can eliminate the requirement for a separate collection device to collect exudate from the wound because the exudate is collected and retained within the volume under the cover. In these embodiments, the interface member is sealed to the body by the sealing means and exudate from the wound flows from the wound through the flow control means in the interface member into the volume of the cover above the interface member. The flow control means do not allow the exudate to flow back into the area of the wound under the interface member. Thus, this type of device could reduce the expense involved in wound treatment by eliminating the need for the collection device. This treatment device also removes exudate from the presence of the wound to aid in wound healing. It is also possible for this type of treatment device to be disposable. Further, some embodiments of the treatment device allow for physical access to the wound without the need for removing the treatment device from the body. In these embodiments, the lid member may be removed from the cup body member of the cover, exposing the area of the wound if an interface member is not utilized. This embodiment of the device could enhance patient comfort because it would not be necessary to remove the sealing means to access the wound. In addition, because access is simple and quickly obtained, the present invention may also decrease the cost of wound treatment by reducing the time required of healthcare practitioners to be involved in wound treatment. The present invention should also be relatively inexpensive to produce, while meeting the needs described above. Finally, as can be observed from the foregoing discussion, the present invention has great flexiblity. In various embodiments, it may be used with or without the interface member, as well as with or without the removable lid feature.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION

Figure 1:
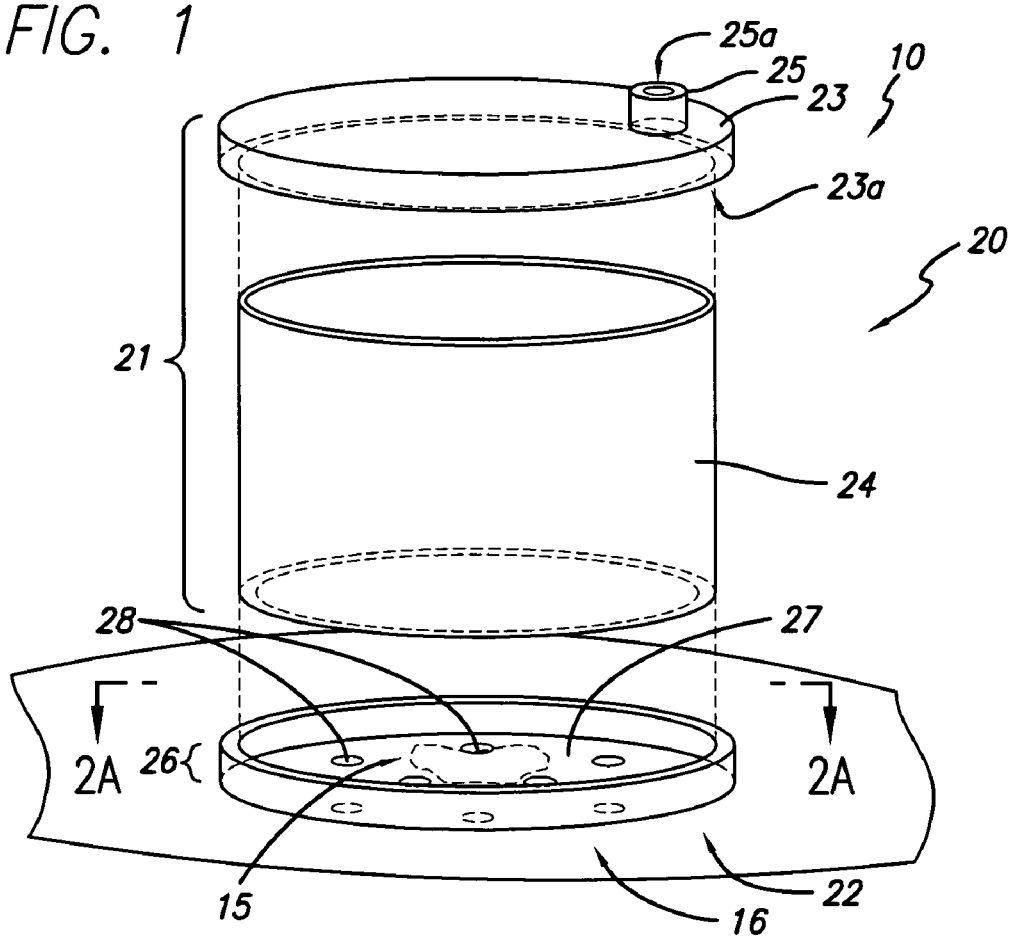
FIG. 1 is an exploded perspective view of an embodiment of a cover comprising the present invention, as such cover would appear from above the body of a patient while the cover is positioned on the body.

In accordance with the present invention, a wound treatment appliance is provided for treating a wound by applying reduced pressure (i.e., pressure that is below ambient atmospheric pressure) to the wound in a controlled manner for a selected time period in a manner that overcomes the disadvantages of currently existing apparatus. One embodiment of a first version of the invention is the treatment appliance 10 illustrated in FIG. 1. FIG. 1 is an exploded perspective view of a cover 20 comprising the treatment appliance 10 from the side of and above the cover 20 as it appears when applied to a portion of the body 16 of a patient surrounding a wound 15. In this embodiment, the cover 20 is comprised of a top cup member 21, an interface member 22, and interface attachment means, which are described in more detail below, to attach the interface member 22 to the top cup member 21. This embodiment also comprises sealing means to seal the cover 20 to the portion of the body 16 surrounding the wound 15, which are described in more detail below, and reduced pressure supply means (not illustrated), which are also described in more detail below. The cover 20 is generally sized to be placed over and enclose the wound 15 to be treated. The cover 20 and the sealing means (described in more detail below) allow reduced pressure to be maintained in the volume under the cover 20 at the site of the wound 15 to be treated, as described in more detail below. The reduced pressure supply means are used to operably connect the cover 20 to a reduced pressure supply source (also not illustrated) in a manner so that the reduced pressure supply source provides a supply of reduced pressure to the cover 20, so that the volume under the cover 20 at the site of the wound may be maintained at reduced pressure. It is to be noted, however, that in other embodiments of the present invention, the top cup member 21 may be used for treatment of a wound 15 without the interface member 22. In these embodiments, the top cup member 21 alone is placed over the wound 15 and reduced pressure is applied to the volume under the top cup member 21.

Figure 5:
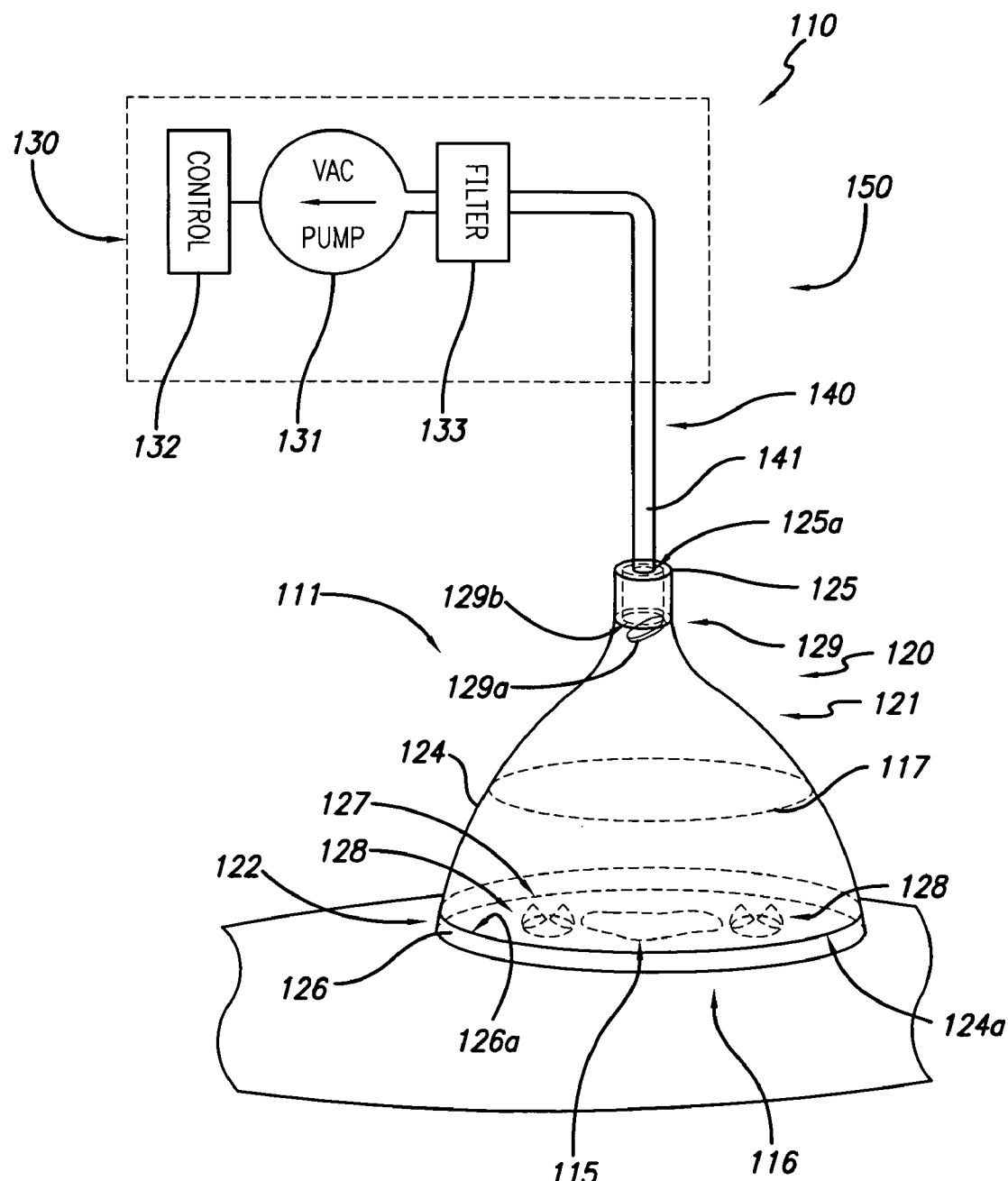
FIG. 5 is a view of an embodiment of a treatment appliance comprising the present invention, in which an embodiment of a treatment device, shown in perspective view, is placed over a wound on a body, and in which an embodiment of a vacuum system, depicted generally and shown in schematic elevation view, provides reduced pressure within the volume under a cover comprising the treatment device.

The embodiment of the top cup member 21 of the cover 20 illustrated in FIG. 1 is further comprised of a lid member 23 and a cup body member 24. In this embodiment, the lid member 23 is removably or permanently attached to the cup body member 24 using lid attachment means, which may be substantially the same as any of the interface attachment means, which are described in more detail below. While the lid member 23 is attached to the cup body member 24, the lid attachment means provides a gas-tight and liquid-tight seal so that reduced pressure may be maintained in the volume under the cover 20 in the area of the wound 15. In the embodiment illustrated in FIG. 1, the top cup member 21 is approximately cylindrical in shape. In other embodiments of this first version of the present invention, the top cup member 21 may be of almost any shape or combination of shapes, as long as the open end 23a of the lid member 23 is of a size and shape adapted to fit against a portion of the surface of the cup body member 24 in a manner so that an airtight and liquid-tight seal can be maintained by the use of the lid attachment means, as described in more detail below. For example, as illustrated in FIG. 5, the top cup member 121 of the cover 120 may be approximately cup-shaped, having an interface member 122 disposed on its bottom surface. As other examples, the cover 20, 120 may be cubical, spherical, spheroidal, hexahedral, polyhedral, or arcuate in shape, or may be comprised of any combination of such shapes, in other embodiments. Thus, referring again to FIG. 1 as an example, the lid member 23 may also be shaped approximately as a hemisphere or a cone in other embodiments. As another example, in yet other embodiments, the cup body member 24 and the open end 23a of the lid member 23 may have a cross-section of approximately elliptical, square, rectangular, polygonal, arcuate or other shape or combination of all such shapes. The preferred shape and size of the top cup member 21, 121, as well as the size and shape of any lid member 23 comprising it, are dependent upon the materials comprising the cover 20, 120, the thickness of the cover 20, 120, the nature of the wound to be treated, the size, shape and contour of the portion of the body to be covered by the cover 20, 120, the magnitude of the reduced pressure to be maintained under the cover 20, 120, the size, shape and other aspects of the interface portion 22, 122, the individual preferences of the user of the cover 20, 120, and other factors related to access to the wound 15, the sealing means, and the reduced pressure supply means, as described in more detail below.

Figure 2A:
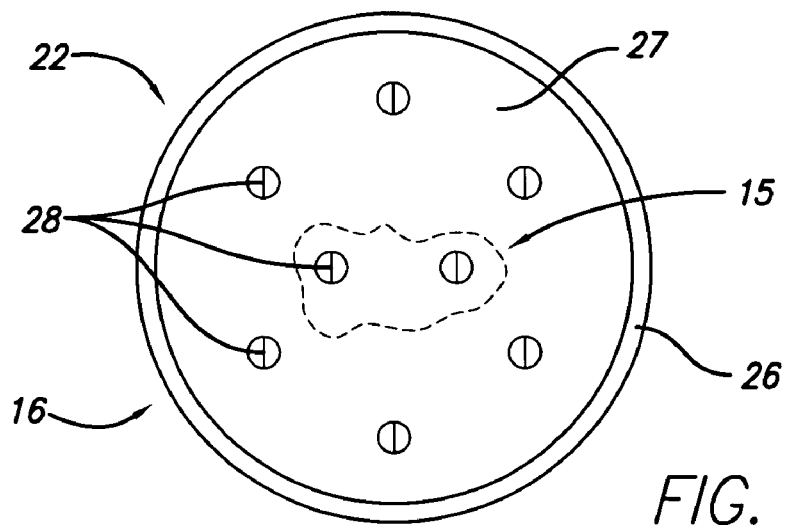
FIG. 2A is an plan view of the interface member of the embodiment of the cover illustrated in FIG. 1, as taken along the lines 2A-2A of FIG. 1.
Figure 2B:
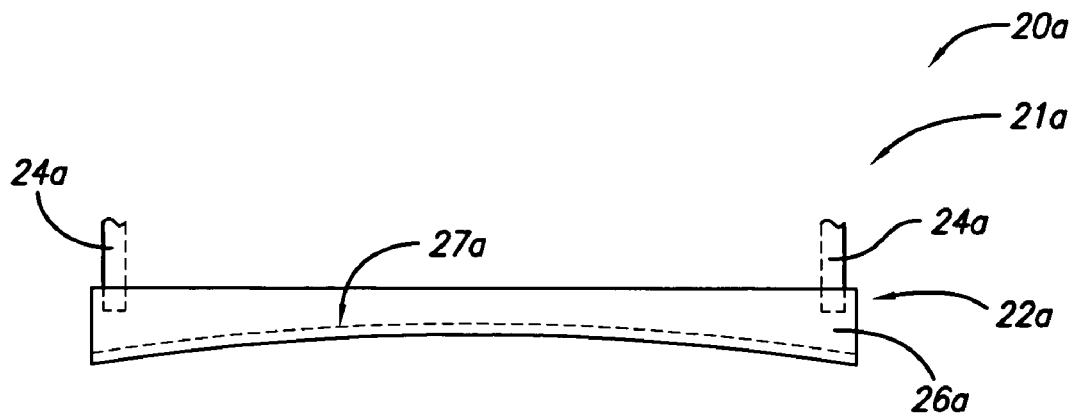
FIG. 2B is an elevation view of another embodiment of an interface member.

In the embodiment of the cover 20 illustrated in FIG. 1, the lid member 23 may be detached from the cup body member 24. This allows the user of the appliance 10 to have access to the area of the wound 15 without having to break the sealing means used to operably seal the cover 20 to the portion of the body 16 surrounding the wound 15. The ability to access the wound 15 in this manner results in more efficient use of the time of healthcare practitioners and less discomfort to patients. It is to be noted that in other embodiments, the lid member 23 and the cup body member 24 may be permanently attached together or may be formed as a single piece. For example, the top cup member 121 of the cover 120 of FIG. 5 does not have a detachable lid member, but is instead formed as a single piece. In these embodiments, and referring to the cover 20 of FIG. 1 as an example, the lid member 23 and the cup body member 24 may be fabricated as a single piece, such as by injection molding, or they may be attached together by any appropriate means, such as by welding, fusing, adhesives, glues, bolts, screws, pins, rivets, clamps, or other fasteners or means or combinations of all such means. In the embodiment of the present invention illustrated in FIG. 1, the lid member 23 and the cup body member 24 are each constructed of a material that is rigid enough to support the cover 20 away from the wound 15. Thus, the lid member 23 and the cup body member 24 of the cover 20 may be comprised of almost any rigid or semi-rigid medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the cover 20 away from the wound 15. For example, the lid member 23 and the cup body member 24 may each be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. It is to be noted that in various embodiments of this first version of the invention, the lid member 23 and the cup body member 24 may be constructed in whole or in part of gas-permeable materials, allowing limited amounts of oxygen to penetrate the lid member 23 and the cup body member 24 so that the portion of the body under the cover 20 in the area of the wound 15 can "breathe." In some embodiments, all portions of the top cup member 21 are preferably constructed of one type of semi-rigid material, such as polypropylene. In other embodiments, the top cup member 21 may be constructed of more than one material. For example, the lid member 23 may be constructed of silicone and the cup body member 24 of the cover 20 may be comprised of polyvinyl chloride, so that the lid member 23 may be stretched enough to overlap and seal against the outer edge of the cup body member 24 to form an operable seal, as described in more detail below. The preferred wall thickness of the cover 20 and its various component parts is dependent upon the size and shape of the cover 20, the size, shape and contour of the portion of the body to be covered by the cover 20, the magnitude of the reduced pressure to be maintained under the cover 20, the materials comprising the cover 20, and the individual preferences of the user of the cover 20. For example, in the embodiment of the cover 20 illustrated in FIG. 1, for a top cup member 21 constructed entirely of a silicone blend and having an approximate diameter of 4 inches and an approximate height of 3 inches, the preferred wall thickness of the top cup member 21 is in the range from $\frac{1}{32}$ inches to $\frac{3}{8}$ inches. It is to be noted that in other embodiments the wall thickness of the various portions of the top cup member 21 may vary from embodiment to embodiment, as well as from portion to portion of the top cup member 21. Generally, the top cup member 21 of the illustrated embodiment may be constructed using any suitable means currently known in the art or that may be developed in the art in the future. For example, a top cup member 21 constructed entirely of a silicone blend may be manufactured by means of injection molding. As another example, embodiments of covers 20 constructed of different types of materials may be constructed in the manner described above in this paragraph. It is to be noted that embodiments of the top cup member 121 comprised of one piece, without separate lid member and cup body member as illustrated by the cover 120 of FIG. 2, the top cup member may be constructed of substantially the same materials, have the same wall thicknesses, and be constructed in substantially the same manner as described above in this paragraph.

In some embodiments of this first version of the present invention, as illustrated in FIG. 1, the cover 20 further comprises a port 25. The port 25 is adapted to be of a size and shape so that the reduced pressure supply means may be operably connected to the top cup member 21 by means of the port 25. When the port 25 is operably connected to the reduced pressure supply means, reduced pressure may be supplied to the volume under the cover 20 at the site of the wound 15 to be treated. Although the port 25 is positioned at a location near one side of the lid member 23 of the enclosure 20 in the embodiment illustrated in FIG. 1, the port 25 may be located at other positions on the top cup member 21 (on either the lid member 23 or the cup body member 24) in other embodiments, as long as the port 25 does not adversely affect the ability of the cup body member 24 to form an operable seal with the lid member 23 or the interface member 22, as described in more detail below. Although the port 25 may be constructed of a material different from the material comprising the remainder of the top cup member 21 in various embodiments of the invention, the port 25 is preferably constructed from the same material comprising the top cup member 21 of the cover 20. In the embodiment of the cover 20 illustrated in FIG. 1, the port 25 is generally cylindrical in shape and is further comprised of an approximately cylindrical channel 25a that extends from the top of the port 25 to the bottom of the port 25. The port 25 of this embodiment is thus able to receive a vacuum system or reduced pressure supply means, which are described in more detail below, adapted to be connected to this shape of port 25 and channel 25a. In other embodiments of this first version of the invention, the port 25 or the channel 25a or both may have different shapes and configurations as may be desired to adapt and connect the port 25 and the channel 25a to the vacuum system or reduced pressure supply means, which are described in more detail below. In some of the embodiments comprising a port 125, as illustrated in the embodiment of the cover 120 of FIG. 5, the top cup member 121 may be further comprised of flow shutoff means (a one-way valve 129 in this embodiment), which are operably connected to the port 125 and described in more detail below. Referring again to FIG. 1 as an example, in other embodiments of this first version of the invention, a means of connecting the top cup member 21 to the reduced pressure supply means (described in more detail below) may be located on the top cup member 21 in lieu of or in conjunction with the port 25. For example, in some embodiments, the port 25 may be combined with a variable descending diameter adapter (commonly referred to as a "Christmas tree" adapter), a luer lock fitting, or other similar adapter or fitting.

In the embodiment of the cover 20 illustrated in FIG. 1, the interface member 22 is removably attached to the cup body member 24 by the interface attachment means (described in more detail below), which are used to make an approximately airtight and liquid-tight seal with the top cup member 21. In the illustrated embodiment, the interface member 22 is comprised of a border portion 26, a membrane portion 27, and membrane flow control means, which are described in more detail below. The membrane portion 27 in the illustrated embodiment has an approximately flat surface and is approximately circular in shape when viewed from above. In other embodiments, the membrane portion 27 may have other shapes. For example, the surface of the membrane portion 27 may have a curved surface, so that it is concave (similar to a concave lens) in shape. In addition, the interface member 22 (and its border portion 26 and membrane portion 27) may be of almost any shape and size, as long as the interface member 22 is of a size and shape adapted so that it fits against a portion of the surface of the top cup member 21 in a manner so that an approximately airtight and liquid-tight seal is maintained by the interface attachment means, as described in more detail below. For example, when viewed from above, the interface member 22 may have an approximately elliptical, square, rectangular, polygonal, arcuate or other shape or combination of all such shapes. As another example, as illustrated in the embodiment of the interface member 22*a* of the cover 20*a* illustrated in FIG. 2B, when viewed from the side, the interface member 22*a* may appear to have an approximately curved surface so that it may rest on portions of the body that have an approximately curved surface. Thus, in the illustrated embodiment, the border portion 26*a* has a generally flat top surface and an approximately concave lower surface bounding the membrane portion 27*a*. Also in this embodiment, the interface member 22*a* is removably attached to the cup body portion 24*a* of the top cup member 21*a* using the interface attachment means, which are described in more detail below. It is to be noted that in some embodiments, as illustrated by the embodiment of the cover 120 in FIG. 5, the top surface of the border portion 126 of the interface member 122 may be positioned adjacent to the bottom surface of the top cup member 121. The preferred shape and size of the interface member 22, 22*a*, 122, as well as the size and shape of the border portion 26, 26*a*, 126 and membrane portion 27, 27*a*, 127 comprising it, are dependent upon the size and shape of the top cup member 21, 21*a*, 121, materials comprising the cover 20, 120, the thickness of the interface member 22, 22*a*, 122, the nature of the wound to be treated, the size, shape and contour of the portion of the body to be covered by the cover 20, 20*a*, 120, the magnitude of the reduced pressure to be maintained under the cover 20, 20*a*, 120, the individual preferences of the user of the cover 20, 20*a*, 120, and other factors related to the sealing means and interface attachment means, as described in more detail below.

In the embodiment of the present invention illustrated in FIG. 1, the border portion 26 is constructed of a material that is rigid enough to support the interface member 22 and the cover 20 away from the wound. Thus, the border portion 26 of the cover 20 may be comprised of almost any rigid or semi-rigid medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the cover 20 away from the wound. For example, the border portion 26 may be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. In the illustrated embodiment, the membrane portion 27 is constructed of a material that is strong enough to support the membrane flow control means, which are described in more detail below. Thus, the membrane portion 27 of the cover 20 may be comprised of almost any rigid, semi-rigid, or flexible medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the membrane flow control means, which are described in more detail below. For example, the membrane portion 27 may be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. It is to be noted that in various embodiments of this first version of the invention, the interface member 22 may be constructed in whole or in part of gas-permeable materials, allowing limited amounts of oxygen to penetrate the interface member 22 so that the portion of the body under the cover 20 can "breathe." In some embodiments, all portions of the interface member 22 are preferably constructed of one type of semi-rigid material, such as polypropylene. In other embodiments, the interface member 22 may be constructed of more than one material. For example, the membrane portion 27 may be constructed of silicone and the border portion 26 of the cover 20 may be comprised of polyvinyl chloride, so that the membrane portion 27 may be more flexible than the border portion 26. The preferred wall thickness of the interface member 22 and its various component parts is generally dependent upon the same parameters as described above for the top cup member 21. Although the interface member 22 need not be constructed of the same materials as the top cup member 21, it is preferred that the interface member 22 be constructed of the same materials as the top cup member 21. Generally, the interface member 22 of the illustrated embodiment may be constructed using any suitable means currently known in the art or that may be developed in the art in the future. For example, an interface member 22 constructed entirely of one material may be manufactured by means of injection molding. As another example, the component parts of an interface member 22 constructed of different types of materials may be attached together by any appropriate means, such as by welding, fusing, adhesives, glues, bolts, screws, pins, rivets, clamps, or other fasteners or other means or combinations of all such means.

Referring to the embodiment of the cover 20 illustrated in FIG. 1, the interface member 22 is further comprised of membrane flow control means, which allow exudate aspirated from the wound 15 to flow into the volume of the top cup member 21, but not in the opposite direction. In the illustrated embodiment, the membrane flow control means is comprised of eight flow control valves 28. It is to be noted that in various embodiments the flow control valves 28 may be any type of valve currently known in the relevant art or that may be developed in the relevant art in the future that is suitable for operation in reduced pressure environments that allows fluids to flow in one direction through the valve, but not in the opposite direction. For example, such valves 28 may generally be comprised of sprung or unsprung flapper or disc-type valves. In the illustrated environment, the flow control valves 28 are comprised of flapper-type valves, which are each further comprised of two flappers that are approximately semi-circular in shape and hinged at their outside edge so that when they fall together they form a seal that only allows fluids to flow in one direction (from the wound 15 to the volume within the top cup member 21 in this embodiment). Although the interface member 22 may have at least one flow control valve 28 in some embodiments, the interface member 22 may have almost any number of flow control valves 28 in other embodiments. For example, as illustrated in FIG. 5, the interface member 122 may be comprised of two flow control valves 128. In embodiments of the present invention comprising flow control valves 28, the preferred number and type of valves 28 is dependent upon the shape and size of the interface member 22, the materials comprising the interface member 22, the thickness of the membrane portion 27, the nature of the wound 15 to be treated, the amount of exudate anticipated, the size, shape and contour of the portion of the body to be covered by the cover 20, the magnitude of the reduced pressure to be maintained under the cover 20, the individual preferences of the user of the cover 20, and other factors related to the sealing means, as described in more detail below. It is to be noted that in some embodiments, the flow control valves 28 may be formed from a single piece with the membrane portion 27, or may be attached to the membrane portion 27 using any suitable means, such as by welding, fusing, adhesives, glues, bolts, screws, pins, rivets, clamps, or other fasteners or means or combinations of all such means. In other embodiments, the membrane flow control means may be comprised of a membrane portion 27 that is constructed in whole or in part of a material that allows fluids to flow in one direction, but not in the opposite direction. In these embodiments, exudate from the wound 15 flows from the wound 15 through the membrane portion 27 (or a portion thereof) to the volume within the top cup member 21, but does not flow in the reverse direction back to the wound 15.

Figure 3:
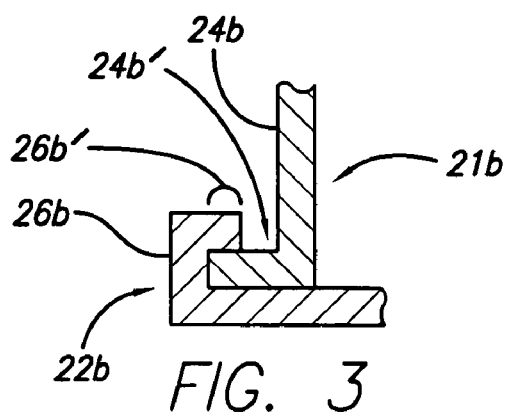
FIG. 3 is an enlarged cross-sectional elevation view of one embodiment of the interface attachment means comprising the present invention.
Figure 4:
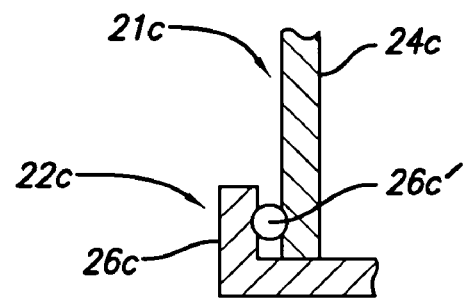
FIG. 4 is an enlarged cross-sectional elevation view of another embodiment of the interface attachment means comprising the present invention.

In various embodiments of this first version of the present invention, the interface attachment means, which may be used to removably or permanently attach the interface member 22 to the top cup member 21, may be any suitable means currently known in the relevant art or developed in the relevant art in the future that may be used to create an airtight and liquid-tight seal (sometimes referred to herein as an "operable seal") between the interface member 22 and the top cup member 21. For example, in the embodiment illustrated in FIG. 3, which is an enlarged cross-sectional elevation view of an interface attachment means, the border portion 26b is constructed of a semi-rigid material (such as silicone) and has a lip portion 26b' that extends around the perimeter of the interface member 22b. The cup body member 24b of the top cup member 21b also has a lip portion 24b' adjacent to the bottom edge of the cup body member 24b that extends around the perimeter of the bottom edge of the cup body member 24b. In this embodiment, the interface attachment means is comprised of the lip portion 26b' of the interface member 22b being stretched over the lip portion 24b' of the top cup member 21, so that the lip portions are joined tightly together to form an operable seal. As another example, as illustrated in FIG. 4, the interface attachment means may be comprised of an o-ring (or gasket or similar sealing means) 26c' that is positioned in a groove extending around the perimeter of the border portion 26c or the cup body member 24c or both, so that the o-ring 26c' forms an operable seal between the top cup member 21c and the interface member 22c. Referring again to FIG. 1 as an example, in still other embodiments, the exterior bottom portion of the cup body member 24 may be threaded and the interior bottom portion of the border portion 26 of the interface member 22 may be of a structure to receive such threads, so that an operable seal is created when the cup body member 24 is screwed into the interface member 22. In yet other embodiments, as illustrated in FIG. 5, the interface attachment means may be comprised of a magnetic strip (not shown) attached to the bottom surface 124a of the cup body member 124 of the top cup member 121 and to the top surface 126a of the border portion 126 of the interface member 122, so that such surfaces abut against one another in the manner illustrated in FIG. 5 when the surfaces are attracted by magnetic force, creating an operable seal. Further, the interface attachment means may be comprised of a washer, gasket, o-ring or similar structure (not shown) attached to the bottom surface 124a of the cup body member 124 of the top cup member 121 or to the top surface 126a of the border portion 126 of the interface member 121, or both, so that such surfaces abut against one another in the manner illustrated in FIG. 5, creating an operable seal. In these embodiments, the top cup member 121 may be held in place against the interface member 122 by means of clips, brackets, pins, clamps, clasps, adhesives, adhesive tapes, quick-release or other fasteners, or combinations of such means. In addition, many types of sealing means that may be used to removably attach components of kitchenware-type items together may by used as the interface attachment means. It is also to be noted that in other embodiments the interface attachment means may be comprised of means to permanently attach the interface member 22 to the top cup member 21 or of forming the interface member 22 and the top cup member 21 as a single piece. In these embodiments, and referring to the cover 20 of FIG. 1 as an example, the interface member 22 and the top cup member 21 may be fabricated as a single piece, such as by injection molding, or they may be attached together by any appropriate means, such as by welding, fusing, adhesives, glues, bolts, screws, pins, rivets, clamps, or other fasteners or means or any combinations of all such means. Referring again to FIG. 1 as an example, it is to be noted that the lid attachment means that may be used to removably or permanently attach the lid member 23 to the cup body member 21 may have substantially the same structure, features, characteristics and operation as any or all of the embodiments comprising the interface attachment means described above.

An embodiment of a second version of the present invention is the treatment appliance 110 illustrated in FIG. 5. In this embodiment, the treatment appliance 110 is comprised of a treatment device 111 and a vacuum system, generally designated 150, which is operably connected to, and provides a supply of reduced pressure to, the treatment device 111. Also in this embodiment, the treatment device 111 is comprised of a cover 120. In addition, in this embodiment, the vacuum system 150 is further comprised of a reduced pressure supply source, generally designated 130, which is illustrated schematically and described in more detail below, and reduced pressure supply means, generally designated 140, which are described in more detail below. Also in this embodiment, the reduced pressure supply means 140 are used to connect the reduced pressure supply source 130 to the cover 120 in a manner so that reduced pressure is supplied to the volume under the cover 120 at the site of the wound 115 to be treated, as described in more detail below. In the embodiment of the second version of the invention illustrated in FIG. 5, the illustrated cover 120 is comprised of a top cup member 121, an interface member 122, and interface attachment means to removably attach the top cup member 121 to the interface member 122. In the illustrated embodiment, the interface attachment means is comprised of a magnetic strip (not shown) on the top surface 126a of the border portion 126 of the interface member 122 and a magnetic strip (not shown) on the bottom surface 124a of the cup body member 124 of the top cup member 121. An operable seal is formed between the interface member 122 and the top cup member 121 by the magnetic attraction of the magnetic strips. In other embodiments, the interface attachment means may be comprised of any of the interface attachment means of the first version of the present invention illustrated and described above in connection with FIG. 1 through FIG. 5. Alternatively, the interface member 122 and the top cup member 121 may be formed as a single piece or permanently attached, as illustrated and described above in connection with FIG. 1 through FIG. 5. It is to be noted that in this and other embodiments of this second version of the invention, the cover 120 may have substantially the same structure, features, characteristics and operation as any embodiment of any of the covers 20, 20a, 120 of the first version of the invention described above and illustrated in connection with FIG. 1 through FIG. 5. It is also to be noted that in other embodiments of the present invention, the top cup member 121 may be used for treatment of a wound 115 without the interface member 126. In these embodiments, the top cup member 121 alone is placed over the wound 115 and reduced pressure is applied to the volume under the top cup member 121.

In the various embodiments of this second version of the present invention, as illustrated in FIG. 5, the interface member 122 of the cover 120 may be comprised of a semi-rigid material and the sealing means may be comprised of the suction of the interface member 122 against the portion 116 of the body adjacent to the interface member 122 of the cover 120, such suction being produced by the presence of reduced pressure in the volume under the cover 120 at the site of the wound 115. In other embodiments, the sealing means may be comprised of an adhesive, an adhesive tape, lanolin, or other sealant, or any combination of such means, that is disposed between the interface member 122 and the portion 116 of the body adjacent to the interface member 122 or disposed over the interface member 122 and the portion of the body outside the perimeter of the interface member 122. In yet other embodiments, the sealing means may be comprised of a material (not illustrated) that is positioned approximately over the cover 120 and wrapped around the portion 116 of the body on which the cover 120 is positioned. This material is used to hold the cover 120 against the adjacent portion 116 of the body. For example, if the wound 115 were on the patient's leg, an elastic bandage or adhesive tape may be wrapped over the cover 120 and around the leg.

In the embodiment illustrated in FIG. 5, the reduced pressure supply source 130 of the vacuum system 150, which produces a source of reduced pressure or suction that is supplied to the cover 120, is comprised of a vacuum pump 131, a control device 132, and a filter 133. Although the preferred means of producing the reduced pressure or suction is a vacuum pump 131 in this embodiment, in other embodiments of this second version of the invention other means may be used, such as an outlet port of a centralized hospital vacuum system. In the illustrated embodiment, predetermined amounts of suction or reduced pressure are produced by the vacuum pump 131. The vacuum pump 131 is preferably controlled by a control device 132, such as a switch or a timer that may be set to provide cyclic on/off operation of the vacuum pump 131 according to user-selected intervals. Alternatively, the vacuum pump 131 may be operated continuously without the use of a cyclical timer. In addition, in some embodiments the control device 132 may provide for separate control of the level of reduced pressure applied to the volume under the cover 120 at the site of the wound 115 and the flow rate of fluid aspirated from the wound 115, if any. In these embodiments, relatively low levels of reduced pressure may be maintained at the site of the wound 115 in the volume under the treatment device 111, while still providing for the removal of a relatively large volume of exudate from the wound 115. A filter 133, such as a micropore filter, is preferably attached to the inlet of the vacuum pump 131 to prevent potentially pathogenic microbes or aerosols from contaminating, and then being vented to atmosphere by, the vacuum pump 131. In other embodiments, the filter 133 may also be a hydrophobic filter that prevents any exudate from the wound 115 from contaminating, and then being vented to atmosphere by, the vacuum pump 131. It is to be noted that in other embodiments of the invention, the reduced pressure supply source 130 may not have a filter 133 or a control 132 or any combination of the same.

In other embodiments of the second version of the invention, the reduced pressure supply source 130 of the vacuum system 150, may be comprised of a small, portable vacuum pump 131. In some of these embodiments, a filter 133 or a power source (not illustrated), or both, may also be contained within the housing for the portable vacuum pump 131. In these embodiments, the portable vacuum pump 131 is preferably controlled by a control device 132 that is also located within the housing for the portable vacuum pump 131, which may provide substantially the same functions as the control device 132 described above. Except for its smaller size, the portable vacuum pump 131 may operate in substantially the same manner as the vacuum pump 131 described above. Also, in these embodiments, the filter 133 may have the same structure, features, characteristics and operation, and provide substantially the same functions, as the filter 133 described above. In some of these embodiments, the filter 133 may be rigidly connected to the portable vacuum pump 131. The power source may be any source of energy currently known in the art or that may be developed in the art in the future that may be used to power the portable vacuum pump 131. For example, in some embodiments, the power source may be a fuel cell, battery or connection to a standard wall electrical outlet.

In the embodiment of the second version of the invention illustrated in FIG. 5, the reduced pressure supply means 140 of the vacuum system 150, which are used to connect the reduced pressure supply source 130 to the cover 120 so that reduced pressure is supplied to the volume under the cover 120 at the site of the wound 115, is comprised of at least one tubing member 141. In this embodiment, the at least one tubing member 141 is sufficiently flexible to permit movement of the at least one tubing member 141, but is sufficiently rigid to resist constriction when reduced pressure is supplied to the cover 120 or when the location of the wound 115 is such that the patient must sit or lie upon the at least one tubing member 141 or upon the treatment device 111. In the embodiment illustrated in FIG. 5, the at least one tubing member 141 is connected to the cover 120 by inserting one end of the at least one tubing member 141 into an opening 125a of a port 125 of the cover 120. In this embodiment, the at least one tubing member 141 is held in place in the opening 125a by means of an adhesive. It is to be noted that in other embodiments of this second version of the invention, the at least one tubing member 141 may be connected to the port 125 of the cover 120 using any suitable means currently known in the art or developed in the art in the future. Examples include variable descending diameter adapters (commonly referred to as "Christmas tree" adapters), luer lock fittings and adapters, clamps, and combinations of such means. Alternatively, the port 125 and the at least one tubing member 141 may be fabricated as a single piece. Similar means may be used to connect the other end of the at least one tubing member 141 to the vacuum pump 131 or other reduced pressure supply source 130 providing the reduced pressure.

In the embodiment of the second version of the present invention illustrated in FIG. 5, the treatment device 111 functions to actively draw fluid or exudate from the wound 115 through two flow control valves 128 positioned on the membrane portion 127 of the interface member 122 into the interior volume of the cover 120. In this embodiment, it is generally desirable to collect exudate in the interior volume of the cover 120, but not to allow the exudate to flow into the reduced pressure supply means 140 in order to prevent clogging of the vacuum pump 131. In addition, it is desirable to halt or inhibit the supply of reduced pressure to the cover 120 in the event that the exudate aspirated from the wound 115 exceeds a predetermined quantity. Further, it is desirable to interrupt the application of suction to the cover 120 to prevent exsanguination in the unlikely event a blood vessel ruptures under the cover 120 during treatment. If, for example, a blood vessel ruptures in the vicinity of the cover 120, a shutoff mechanism would be useful to prevent the vacuum system 150 from aspirating any significant quantity of blood from the patient. As a result, the top cup member 121 in the illustrated embodiment is further comprised of flow shutoff means. In this embodiment, the flow shutoff means is comprised of a flapper-type valve 129, which is generally comprised of a flapper 129a that is hinged to an interior surface of the port 125 and seats against a stop 129b. The flapper 129a is buoyant when compared to the exudate, so that it floats upon the exudate as the level of exudate in the volume of the cover 120 rises to the level of the flapper valve 129. The flapper 129a is, however, heavy enough not to be drawn against the stop 129b when reduced pressure is applied to the cover 120 by the vacuum system 150. Thus, as the exudate level rises to the level of the stop 129b, the flapper 129a floats upon the exudate until the flapper 129a seats against the stop 129b, which seals the cover 120 so that reduced pressure is no longer supplied to the cover 120 by the vacuum system 150. In other embodiments, the flow shutoff means may be comprised of almost any other type of shutoff valve currently known in the relevant art or that may be developed in the relevant art in the future that is suitable for this purpose and use in a reduced pressure environment. Another example of such valve is a float valve, wherein a float ball floats upon the exudate so that the float ball seals against a seat when the level of exudate reaches a predetermined level. All such valves are well known in the relevant art. In other embodiments, other types of mechanisms may also be employed to detect the liquid level within the cover 120 in order to arrest operation of the vacuum system 150. In addition, in various embodiments of this second version of the invention, the flow shutoff means may be comprised of any means that enables the vacuum system 150 to halt the supply of reduced pressure to the cover 120 at any time that the volume of exudate from the wound 115 exceeds a predetermined amount. Such means may include mechanical switches, electrical switches operably connected to the vacuum system controller 132, optical, thermal or weight sensors operably connected to the vacuum system controller 132, and any other means that are currently known in the relevant art or that may be developed in the relevant art in the future.

In some embodiments of this second version of the invention, the treatment device 111 further comprises tissue protection means (not illustrated) to protect and strengthen the surface tissue of the portions 116 of the body that are adjacent to the cover 120. The tissue protection means protects such tissue by preventing abrasion and maceration of the tissue. Preferably, the tissue protection means is a hydrocolloid material, such as COLOPAST Hydrocolloid 2655 anhydrous lanolin, or any combination of such hydrocolloid materials. More preferably, the tissue protection means is COLOPAST Hydrocolloid 2655. The tissue protection means may be applied to the body tissue to be protected, or it may be applied to the surface of the cover 120 that is to be in contact with the body tissue 116, or both, prior to placing the cover 120 over the wound 115. It is to be noted that application of the tissue protection means to the body tissue 116 that is adjacent to the cover 120 at the site of the wound 115 may only entail application of the tissue protection means to the parts of the body tissue 116 adjacent to the cover 120 that require such protection.

Referring to FIG. 5, a method of using the treatment appliance 110 of the illustrated embodiment is also disclosed. In this example, the cover 120 is removed from an aseptic package in which it is stored. The various component parts of the cover are operably sealed together. For example, in the illustrated embodiment, the top cup member 121 is operably sealed to the interface member 122. In embodiments where the top cup member 21 further comprises a lid member 23 and a cup body member 24, as illustrated in FIG. 1, the lid member 23 and the cup body member 24 are also operably sealed together. Referring again to FIG. 5, this sealing of the component parts of the cover 120 may occur before, during or after the cover 120 is placed over the wound 115. The cover 120 is placed over and encloses the wound 115. The cover 120 is connected to the vacuum system 150 by means of the port 125 on the cover 120 either before, after or during the placement of the cover 120 over the wound 115. Where it is deemed necessary by the user of the treatment appliance 110, tissue protection means, as described above, may be placed on a portion of the cover 120, on the body tissue to be protected, or both, prior to placing the cover 120 over the wound 115. Reduced pressure is then supplied to the cover 120 by the vacuum system 150. In the illustrated embodiment, when reduced pressure is applied to the volume under the cover 120 at the site of the wound 115, the cover 120 is drawn downward by the reduced pressure so that the cover 120 is drawn tightly against the surface of the adjacent portion 116 of the body, thus forming an operable seal between the cover 120 and the portion 116 of the body adjacent to the cover 120. References to an "operable seal" and "sealing means" herein refer generally to a seal that may be made gas-tight and liquid-tight for purposes of the reduced pressure treatment of the wound 115. It is to be noted that this seal need not be entirely gas-tight and liquid-tight. For example, the operable seal may allow for a relatively small degree of leakage, so that outside air may enter the volume under the cover 120 at the site of the wound 115, as long as the degree of leakage is small enough so that the vacuum system 150 can maintain the desired degree of reduced pressure in the volume under the cover 120 at the site of the wound 115. As another example, the operable seal formed by the cover 120 may not be solely capable of maintaining the reduced pressure in the volume under the cover 120 at the site of the wound 115 due to the shape of the body portion 116 at the site of the wound 115, due to the orientation of the wound 115, or due to some other reason. In these cases, as well as other cases, it may be necessary or desirable to provide other sealing means (not illustrated), which are described in more detail above. In some embodiments of the second version of the present invention comprising a lid member 23, as illustrated by the cover 20 of FIG. 1, the method may also comprise one or more of the steps of halting the application of reduced pressure to the cover 20, removing the lid member 23 from the cup body member 24, attending to the wound 115, re-attaching the lid member 23 to the cup body member 24, and then reapplying reduced pressure to the volume under the cover 20 in the area of the wound 115. In yet other embodiments, and referring again to FIG. 5, the method may comprise one or more of the steps of monitoring the fluid level 117 in the volume within the cover 120, halting the application of reduced pressure to the cover 120 when the fluid level 117 reaches a predetermined level, removing the fluid in the volume within the cover 120, and reapplying reduced pressure to the volume under the cover 20 in the area of the wound 115. In the preferred embodiments of this second version of the invention, the reduced pressure maintained in the volume under the cover 120 at the site of the wound 115 is in the range from approximately 20 mm of Hg below atmospheric pressure to approximately 125 mm of Hg below atmospheric pressure. In yet other embodiments, the reduced pressure is applied to the cover 120 in a cyclic nature, the cyclic nature providing alternating time periods of application of reduced pressure and non-application of reduced pressure. In various embodiments, the method also comprises the step of maintaining reduced pressure in the volume under the cover 120 at the site of the wound 115 until the wound 115 has progressed toward a selected stage of healing.

Figure 6:
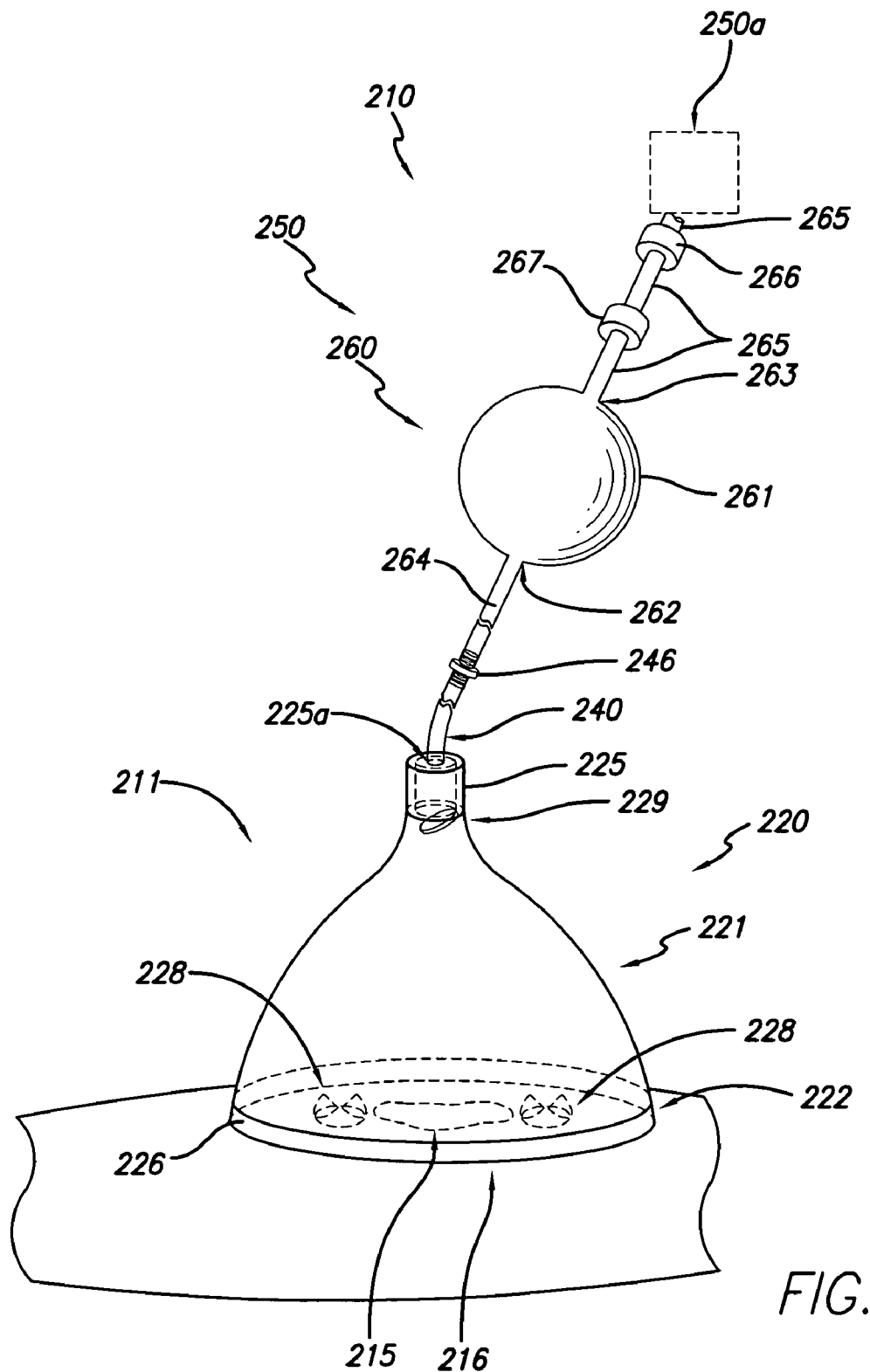
FIG. 6 is a view of an embodiment of a treatment appliance comprising the present invention, in which an embodiment of a treatment device, shown in perspective view from the side of and above the treatment device, is positioned over a wound on a body, and in which an embodiment of a vacuum system, shown in elevational view, provides reduced pressure within the volume under a cover comprising the treatment device.

An embodiment of a third version of the invention is the treatment appliance 210 illustrated in FIG. 6. In this embodiment, the treatment appliance 210 is comprised of a treatment device 211 and a vacuum system, generally designated 250, operably connected to, and providing a supply of reduced pressure to, the treatment device 211. In addition, in this embodiment, the vacuum system 250 is further comprised of a reduced pressure supply source, generally designated 260, which is described in more detail below, and reduced pressure supply means 240, which are described in more detail below. Also in this embodiment, the treatment device 211 is further comprised of a cover 220, which generally has substantially the same structure, features, and characteristics as the embodiment of the cover 120 illustrated and described above in connection with FIG. 5. It is to be noted, however, that in other embodiments of this third version of the invention, the cover 220 may have substantially the same structure, features, characteristics and operation as any embodiment of all of the covers 20, 20a, 120 of the first and second versions of the invention described above and illustrated in connection with FIG. 1 through FIG. 5. In the embodiment illustrated in FIG. 6, the cover 220 is placed over and encloses a wound 215. In the illustrated embodiment, the cover 220 may be sealed to the adjacent portions 216 of the body using any of the sealing means or operable seals described above and illustrated in connection with FIG. 5.

In the embodiment of the third version of the invention illustrated in FIG. 6, the vacuum system 250 is generally comprised of a suction bulb 261 having an inlet port 262 and an outlet port 263, a bulb connection tubing member 264, an exhaust tubing member 265, an exhaust control valve 266, a filter 267, and a supplemental vacuum system (illustrated schematically and generally designated 250a). In this embodiment, the suction bulb 261 is a hollow sphere that may be used to produce a supply of reduced pressure for use with the treatment device 211. In addition, in some embodiments, the suction bulb 261 may also be used to receive and store exudate aspirated from the wound 215. The inlet port 262 of the suction bulb 261 is connected to one end of the bulb connection tubing member 264, which is connected to the reduced pressure supply means 240, a tubing member in this embodiment, by means of a connector 246. The connection tubing member 264 is connected to the reduced pressure supply means 240 in a manner so that the interior volume of the suction bulb 261 is in fluid communication with the volume under the cover 220 in the area of the wound 215. In this embodiment, the bulb connection tubing member 264 and the reduced pressure supply means 240 are sufficiently flexible to permit movement of the bulb connection tubing member 264 and the reduced pressure supply means 240, respectively, but are sufficiently rigid to resist constriction when reduced pressure is supplied to the cover 220 or when the location of the wound 215 is such that the patient must sit or lie upon the bulb connection tubing member 264, upon the reduced pressure supply means 240, or upon the treatment device 311. The outlet port 263 of the suction bulb 261 is connected to the exhaust tubing member 265. In this embodiment, the exhaust tubing member 265 is sufficiently flexible to permit movement of the exhaust tubing member 265, but is sufficiently rigid to resist constriction when reduced pressure is supplied to the cover 220. The inlet port 262 of the suction bulb 261 may be connected to the bulb connection tubing member 264 and the outlet port 263 of the suction bulb 261 may be connected to the exhaust tubing member 265 using any suitable means, such as by welding, fusing, adhesives, clamps, or any combination of such means. In addition, in some embodiments, which are the preferred embodiments, the suction bulb 261, the bulb connection tubing member 264, and the exhaust tubing member 265 may be fabricated as a single piece. In the illustrated embodiment, the exhaust control valve 266 and the filter 267 are operably connected to the exhaust tubing member 265. In this embodiment, the exhaust control valve 266 is used to regulate the flow of fluids (gases and liquids) to and from the suction bulb 261 and the supplemental vacuum system 250a. In embodiments of the invention that do not have a supplemental vacuum system 250a, the exhaust control valve 266 regulates flow of fluids to and from the suction bulb 261 and the outside atmosphere. Generally, the exhaust control valve 266 allows fluids to flow out of the suction bulb 261 through the outlet port 263, but not to flow in the reverse direction unless permitted by the user of the appliance 210. Any type of flow control valve may be used as the exhaust control valve 266, as long as the valve 266 is capable of operating in the anticipated environment involving reduced pressure and wound 215 exudate. Such valves are well known in the relevant art, such as sprung and unsprung flapper-type valves and disc-type valves, operating in conjunction with or without ball, gate and other similar types of valves. In this embodiment, the filter 267 is operably attached to the exhaust tubing member 265 between the outlet port 263 of the suction bulb 261 and the exhaust control valve 266. The filter 267 prevents potentially pathogenic microbes or aerosols from contaminating the exhaust control valve 266 (and supplemental vacuum system 250a), and then being vented to atmosphere. The filter 267 may be any suitable type of filter, such as a micropore filter. In other embodiments, the filter 267 may also be a hydrophobic filter that prevents any exudate from the wound 215 from contaminating the exhaust control valve 266 (and the supplemental vacuum system 250a) and then being vented to atmosphere. In still other embodiments, the filter 267 may perform both functions. It is to be noted, however, that the outlet port 263, the exhaust control valve 266, the filter 267, or any combination of the exhaust control valve 266 and the filter 267, need not be utilized in connection with the vacuum system 250 in other embodiments of the invention.

In some embodiments of the third version of the invention illustrated in FIG. 6 that do not utilize a supplemental vacuum system 250a, the suction bulb 261 may be used to produce a supply of reduced pressure in the following manner. First, the user of the appliance 210 appropriately seals all of the component parts of the appliance 210 in the manner described herein. For example, the top cup member 221 of the cover 220 is operably sealed to the interface member 222 of the cover 220, and the cover 220 is placed over and encloses the wound 215. At least a portion of the interface member 222 is sealed (or placed adjacent) to the adjacent portions 216 of the body, and the reduced pressure supply means 240 is connected to the bulb connection tubing member 264 by means of the connector 246. The user then opens the exhaust control valve 266 and applies force to the outside surface of the suction bulb 261, deforming it in a manner that causes its interior volume to be reduced. When the suction bulb 261 is deformed, the gas in the interior volume is expelled to atmosphere through the outlet port 263, the exhaust tubing member 265, the filter 267, and the exhaust control valve 266. The user then closes the exhaust control valve 266 and releases the force on the suction bulb 261. The suction bulb 261 then expands, drawing gas from the area of the wound 215 under the treatment device 211 into the suction bulb 261 and causing the pressure in such area to decrease. To release the reduced pressure, the user of the appliance 210 may open the exhaust control valve 266, allowing atmospheric air into the interior volume of the suction bulb 261. The level of reduced pressure may also be regulated by momentarily opening the exhaust control valve 266.

The suction bulb 261 may be constructed of almost any fluid impermeable flexible or semi-rigid material that is suitable for medical use and that can be readily deformed by application of pressure to the outside surface of the suction bulb 261 by users of the appliance 210 and still return to its original shape upon release of the pressure. For example, the suction bulb 261 may be constructed of rubber, neoprene, silicone, or other flexible or semi-rigid polymers, or any combination of all such materials. In addition, the suction bulb 261 may be of almost any shape, such as cubical, ellipsoidal, or polyhedral. The suction bulb 261 may also be of varying size depending upon the anticipated use of the suction bulb 261, the size of the wound treatment device 211, use of a supplemental vacuum system 250a, the level of reduced pressure desired, and the preference of the user of the appliance 210. In the embodiment of the invention illustrated in FIG. 6, the supplemental vacuum system 250a is connected to the exhaust tubing member 265 and is used to provide a supplemental supply of reduced pressure to the suction bulb 261 and treatment device 211. In this embodiment, the supplemental vacuum system 250a may have substantially the same structure, features, characteristics and operation of the various embodiments of the vacuum system 250 of the second version of the invention described above and illustrated in connection with FIG. 5. It is to be noted, however, that the supplemental vacuum system 250a need not be used in connection with the vacuum system 250 in other embodiments of the invention.

Except as illustrated and described above in connection with FIG. 6, the treatment appliance 210 may generally be used in a manner similar to the treatment appliance 110 described above and illustrated in connection with FIG. 5. As a result, except as described herein, the example of how the embodiment of the treatment appliance 110 and the cover 120 described above and illustrated in connection FIG. 5 may be used in treatment of a wound 115 also applies to the embodiment of the appliance 210 of the third version of the invention described above and illustrated in connection with FIG. 6.

What is claimed is:

1. An appliance for administering reduced pressure treatment to a wound on a body, the appliance comprising:
   a cover comprising:
      a top cup member, wherein the top cup member comprises a lid member, a cup body member, and lid attachment means configured to removably attach the lid member to the cup body member;
      an interface member, wherein the interface member comprises flow control means configured to permit exudate from the wound to flow from the wound into the top cup member, but not in the opposite direction; and
      interface attachment means configured to removably attach the top cup member to the interface member;
      wherein the cover is sized to be placed over and enclose the wound and adapted to maintain reduced pressure in the volume under the cover at the site of the wound;
   a seal configured to directly seal the interface member to the body so that reduced pressure may be maintained in the volume under the cover at the site of the wound, the seal being maintainable when the top cup member is removed from the interface member; and
   a reduced pressure supply means configured to provide a supply of reduced pressure from a reduced pressure supply source to the cover.

2. The appliance of claim 1, wherein the cover is cylindrical in shape.

3. The appliance of claim 1, wherein the interface attachment means provides for removable attachment of the top cup member to the interface member, but does not provide for permanent attachment of the top cup member to the interface member.

4. The appliance of claim 1, wherein the interface attachment means comprises an o-ring seal.

5. The appliance of claim 3, wherein a portion of the interface member is of a size and shape adapted to fit tightly against a portion of the top cup member, wherein an operable seal is created between the interface member and the top cup member.

6. The appliance of claim 1, wherein the interface attachment means comprises a magnetic seal.

7. The appliance of claim 1, wherein the interface attachment means provides for permanent attachment of the top cup member to the interface member, but does not provide for removable attachment of the top cup member to the interface member.

8. The appliance of claim 1, wherein the interface member is further comprised of a membrane portion that is disposed approximately adjacent to the body and the flow control means comprises at least one one-way valve operably disposed in the membrane portion.

9. The appliance of claim 1, wherein the interface member is further comprised of a membrane portion that is disposed approximately adjacent to the body and that permits fluid to flow in only one direction, and the flow control means comprises all or a portion of the membrane portion.

10. The appliance of claim 1, wherein the lid attachment means comprises an o-ring seal.

11. The appliance of claim 1, wherein a portion of the lid member is of a size and shape adapted to fit tightly against a portion of the cup body member, wherein an operable seal is created between the lid member and the cup body member.

12. The appliance of claim 1, wherein the lid attachment means comprises a magnetic seal.

13. The appliance of claim 1, wherein the seal is disposed between at least a portion of the interface member and a portion of the body adjacent to the wound.

14. The appliance of claim 1, wherein the interface member defines a perimeter and the seal is disposed at least over a portion of the interface member and at least a portion of the body that is outside of the perimeter of the interface member.

15. The appliance of claim 1, wherein the seal comprises an adhesive.

16. The appliance of claim 1, wherein the seal comprises lanolin.

17. The appliance of claim 1, wherein the cover is configured such that the reduced pressure supplied to the cover operably seals the interface member to the body.

18. The appliance of claim 1, wherein the cover is configured such that the reduced pressure supplied to the cover operably seals the cup body member to the interface member.

19. The appliance of claim 1, wherein the cover is configured such that the reduced pressure supplied to the cover operably seals the lid member to the cup body member.

20. The appliance of claim 1, wherein the interface member is elliptical in shape.

21. The appliance of claim 1, wherein the interface member is rectangular in shape.

22. The appliance of claim 1, wherein the interface member comprises at least one curved portion adapted to be positioned on a portion of the body and configured to approximately match the portion of the body on which the curved portion is positioned.

23. The appliance of claim 1, wherein the reduced pressure supply means comprises at least one conduit.

24. The appliance of claim 1, wherein the cover is configured such that at least a portion of the cover is shaped to approximately match the surface shape of at least a portion of the body covered by the cover.

25. The appliance of claim 1, wherein the lid attachment means comprises one or more clamps.

26. The appliance of claim 1, wherein the lid attachment means comprises one or more mechanical fasteners.

27. The appliance of claim 1, wherein the cover comprises a port configured to be removably attached to the reduced pressure supply means.

28. The appliance of claim 27, wherein the port is provided on the lid member.

29. The appliance of claim 1, wherein the appliance is configured to inhibit the supply of reduced pressure to the cover when an amount of exudate under the cover exceeds a predetermined quantity.

30. The appliance of claim 1, wherein the cover comprises a valve that is configured to inhibit the supply of reduced pressure to the cover when an amount of exudate under the cover exceeds a predetermined quantity.

31. The appliance of claim 8, wherein the membrane portion defines at least one curved surface adapted to be positioned on a portion of the body and configured to approximately match the portion of the body against which the curved surface is positioned.

32. The appliance of claim 8, wherein the membrane portion comprises rubber.

33. The appliance of claim 8, wherein the membrane portion comprises neoprene.

34. The appliance of claim 8, wherein the membrane portion comprises a gas-permeable material.

35. The appliance of claim 8, wherein the membrane portion is configured to allow oxygen to flow therethrough so as to expose a portion of the body under the membrane portion with the oxygen.

36. The appliance of claim 1, further comprising a reduced pressure supply source configured to be connected to the reduced pressure supply means.

37. The appliance of claim 1, wherein the interface attachment means comprises at least one of a clamp, a clasp, and other fastener.

38. The appliance of claim 1, wherein the interface member defines an outer peripheral edge that extends beyond an outer peripheral edge of the cup body member.

39. The appliance of claim 1, wherein the cover is configured so that no portion of the top cup member directly contacts the body when the top cup member is attached to the interface member and the interface member is sealed to the body.

40. The appliance of claim 1, wherein the cover is configured so that no portion of the top cup member directly contacts the seal when the top cup member is removably attached to the interface member and the interface member is sealed to the body.

41. An appliance for administering reduced pressure treatment to a wound on a body, the appliance comprising:
 a cover configured to enclose the wound such that a reduced pressure is provided to the wound, the cover comprising:
  a lid member;
  a body member; and
  an interface member;
 wherein:
  the lid member is configured to be removably and sealingly supported by a first portion of the body member so as to substantially enclose the first portion of the body member when the lid member is supported by the body member;
  the interface member is removably fastenable to a second portion of the body member so as to substantially enclose the second portion of the body member when the body member is removably fastened to the interface member;
  an interior volume is defined within the body member between the interface member and the lid member when the lid member is supported by the body member and the body member is removably fastened to the interface member;
  the interface member is adapted to be sealed to a portion of the body adjacent to the wound and is configured to permit exudate from the wound to flow from the wound into the interior volume and to inhibit the flow of exudate from the interior space into the wound; and
  a port configured to connect the interior volume of the body member to a source of negative pressure.

42. The appliance of claim 41, further comprising a reduced pressure supply source configured to provide a supply of reduced pressure through the port to the interior volume.

43. The appliance of claim 41, further comprising a conduit configured to connect the port to a reduced pressure supply source.

44. The appliance of claim 41, further comprising a seal configured to seal at least a portion of the interface member with a portion of the body adjacent to the wound.

45. The appliance of claim 41, wherein the interface member defines a perimeter and a seal is disposed at least over a portion of the interface member configured to seal with at least a portion of the body that is outside of the perimeter of the interface member.

46. The appliance of claim 44, wherein the seal comprises adhesive.

47. The appliance of claim 44, wherein the seal comprises lanolin.

48. The appliance of claim 41, wherein the cover is configured such that a supply of reduced pressure provided to the cover operably seals the interface member to the body.

49. The appliance of claim 41, wherein the cover is configured such that a supply of reduced pressure provided to the cover operably seals the body member to the interface member.

50. The appliance of claim 41, wherein the cover is configured such that a supply of reduced pressure provided to the cover operably seals the lid member to the body member.

51. The appliance of claim 41, wherein the body member is cylindrical in shape.

52. The appliance of claim 41, wherein the interface member is elliptical in shape.

53. The appliance of claim 41, wherein the interface member is square in shape.

54. The appliance of claim 41, wherein the interface member is rectangular in shape.

55. The appliance of claim 41, wherein the interface member comprises at least one curved portion adapted to be positioned on a portion of the body and configured to approximately match the portion of the body on which the curved portion is positioned.

56. The appliance of claim 41, wherein the cover is configured such that at least a portion of the cover is shaped to approximately match the surface shape of at least a portion of the body covered by the cover.

57. The appliance of claim 41, wherein the lid member is attached to the body member using one or more clamps.

58. The appliance of claim 41, wherein the lid member is attached to the body member using one or more quick release fasteners.

59. The appliance of claim 41, wherein the lid member is attached to the body member using one or more brackets.

60. The appliance of claim 41, wherein the lid member is attached to the body member using one or more mechanical fasteners.

61. The appliance of claim 41, wherein the appliance is configured to inhibit a supply of reduced pressure to the cover when an amount of exudate within the interior space exceeds a predetermined quantity.

62. The appliance of claim 41, wherein the cover comprises a valve that is configured to inhibit a supply of reduced pressure to the cover when an amount of exudate within the interior space exceeds a predetermined quantity.

63. The appliance of claim 41, wherein at least a portion of the interface member comprises rubber.

64. The appliance of claim 41, wherein at least a portion of the interface member comprises neoprene.

65. The appliance of claim 41, wherein at least a portion of the interface member comprises a gas-permeable material.

66. The appliance of claim 41, wherein the interface member is configured to allow oxygen to flow to a portion of the body under the interface member.

67. The appliance of claim 41, wherein the interface member is removably fastenable to a second portion of the body member using a clamp, a clasp, or other fastener.

68. The appliance of claim 41, wherein the interface member sealingly supports the second portion of the body member.

69. The appliance of claim 41, wherein the interface member defines an outer peripheral edge that extends beyond an outer peripheral edge of the body member.

70. The appliance of claim 41, wherein the cover is configured so that no portion of the body member directly contacts the body when the body member is removably fastened to the interface member and the interface member is sealed to the body.

71. The appliance of claim 41, wherein the interface member is configured to remain sealed to the body when the body member is removed from the interface member.

72. An appliance for administering reduced pressure treatment to a wound on a body, the appliance comprising:
 a cover comprising a lid member, a cup body member comprising a lower portion configured to surround the wound and an upper portion defining a volume within the cup body member configured to extend above the body so as not to contact the wound when the cover is positioned on the body, the lid member being configured to be removably and sealingly attached to the cup body member, wherein the cover is sized to be placed over and enclose the wound and adapted to maintain reduced pressure in the volume under the cover at the site of the wound, and wherein the cup body member defines an opening sized and shaped to allow a user to access the wound when the lid member is removed from the cup body member without removing the cup body member from the body;
 an interface member configured to be removably fastened to the lower portion of the cup body member and configured to permit exudate from the wound to flow from the wound into the volume within the cup body member and to inhibit the flow of exudate from the interior within the cup body member into the wound; and
 a port configured to connect the volume of the cup body member to a source of negative pressure;
 wherein the appliance is configured such that when negative pressure is applied through the port, flow is created from the wound through the volume within the cup body member and through the port, said flow being unobstructed between the volume within the cup body member and the lid member when the lid member is attached to the cup body member.

73. The appliance of claim 72, further comprising a reduced pressure supply source configured to provide a supply of reduced pressure through the port to the interior volume.

74. The appliance of claim 72, further comprising a conduit configured to connect the port to a reduced pressure supply source.

75. The appliance of claim 72, further comprising a seal configured to seal at least a portion of the interface member with a portion of the body adjacent to the wound.

76. The appliance of claim 72, wherein the interface member comprises a membrane and a plurality of flow control valves.

77. The appliance of claim 72, wherein the interface member is configured to be removably fastened to the lower portion of the cup body member using a clamp, a clasp, or other fastener.

78. The appliance of claim 72, wherein the interface member defines an outer peripheral edge that extends beyond an outer peripheral edge of the cup body member.

79. The appliance of claim 72, wherein the cover is configured so that no portion of the body member directly contacts the body when the body member is removably fastened to the interface member and the interface member is sealed to the body.

80. The appliance of claim 72, wherein the interface member is configured to remain sealed to the body when the lower portion of the cup body member is removed from the interface member.

* * * * *